United States Patent
Brossat et al.

(10) Patent No.: US 11,517,516 B2
(45) Date of Patent: Dec. 6, 2022

(54) USE OF ESTER DERIVATIVE OF TRYPTOPHAN AS DEODORANT AND/OR PERFUME AGENT

(71) Applicant: L'oreal, Paris (FR)

(72) Inventors: Maude Brossat, Aulnay sous Bois (FR); Philippe Marruedo, Aulnay sous Bois (FR)

(73) Assignee: L'OREAL, Paris (FR)

( * ) Notice: Subject to any disclaimer, the term of this patent is extended or adjusted under 35 U.S.C. 154(b) by 9 days.

(21) Appl. No.: 15/537,131

(22) PCT Filed: Dec. 18, 2015

(86) PCT No.: PCT/EP2015/080696
§ 371 (c)(1),
(2) Date: Jun. 16, 2017

(87) PCT Pub. No.: WO2016/097398
PCT Pub. Date: Jun. 23, 2016

(65) Prior Publication Data
US 2017/0360668 A1    Dec. 21, 2017

(30) Foreign Application Priority Data

Dec. 18, 2014  (FR) ..................... 1462828

(51) Int. Cl.
| A61K 8/49 | (2006.01) |
| A61Q 15/00 | (2006.01) |
| C07D 209/20 | (2006.01) |

(52) U.S. Cl.
CPC .............. A61K 8/492 (2013.01); A61Q 15/00 (2013.01); C07D 209/20 (2013.01)

(58) Field of Classification Search
CPC ....... A61K 8/492; A61Q 15/00; C07D 209/20
See application file for complete search history.

(56) References Cited

U.S. PATENT DOCUMENTS

| 4,634,588 A * | 1/1987 | Moroe ................... A61K 8/678 424/48 |
| 2004/0176436 A1* | 9/2004 | Behl ...................... A61K 31/00 514/419 |
| 2004/0234466 A1* | 11/2004 | Banowski ................ A61K 8/34 424/65 |

FOREIGN PATENT DOCUMENTS

| CN | 102 391 137 A | 3/2012 |
| EP | 0 647 443 A1 | 4/1995 |
| EP | 0 786 247 A1 | 7/1997 |
| FR | 2 944 972 A1 | 11/2010 |
| FR | 2 948 285 A1 | 1/2011 |
| FR | 2 961 097 A1 | 12/2011 |
| JP | H07 178328 A | 7/1995 |
| WO | WO 97/30687 A2 | 8/1997 |
| WO | WO-99/30680 A1 | 6/1999 |
| WO | WO-00/15206 A2 | 3/2000 |
| WO | WO-2006/119283 A2 | 11/2006 |
| WO | WO-2006/119283 A3 | 11/2006 |
| WO | WO-2012/129671 A1 | 10/2012 |

OTHER PUBLICATIONS

RN77521-33-6 (Year: 1984).*
Sliskovic et al (Year: 2009).*
JPH11286423A, Machine Translation (Year: 1999).*
Clogston et al., "Controlling release from the lipidic cubic phase by selective alkylation", Journal of Controlled Release, 102(2005) 441-461.
Galpin et al., "Synthesis of the 105-117 Fragment of a Lysozyme Analogue", Peptides—XXXXIV, vol. 37, No. 17, Jan. 1981, pp. 3031-3036.
Ueda et al., "Regioselective Diversification of a Cardiac Glycoside, Lanatoside C, by Organocatalysis", J. Org. Chem., 2012, 77, 7850-7857.
Torres-Garcia et al., "Side Chain Anchoring of Tryptophan to Solid Supports Using a Dihydropyranyl Handle: Synthesis of Brevianamide F", Int. J. Pept. Res. Ther. (2013) 18:7-19.
Elmegeed et al., "Synthesis and Antidepressant Evaluation of Five Novel Heterocyclic Tryptophan-Hybrid Derivatives", Arch. Pharm. Chem. Life Sci., 2010, 342, 261-267.
Olmos et al., "Scandium(III)-Zeolites as New Heterogeneous Catalysts for Imino-Diels-Alder Reactions", Chem. Eur. J., 2012, 18, 4894-4901.

* cited by examiner

*Primary Examiner* — Jeffrey S Lundgren
*Assistant Examiner* — Ibrahim D Bori
(74) *Attorney, Agent, or Firm* — Polsinelli PC

(57) ABSTRACT

This invention relates to the use of at least one following compound having formula (I), as well as the salts thereof, the optical and geometric isomers thereof, and the solvates thereof, as deodorant agent for treating body odor, preferably underarm odor:

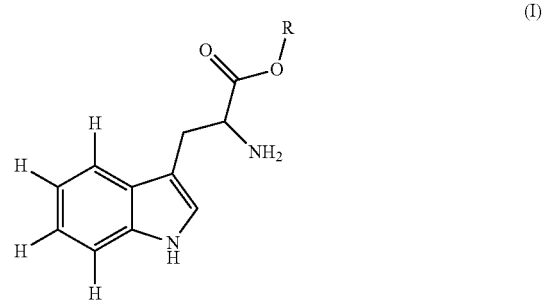

6 Claims, No Drawings

USE OF ESTER DERIVATIVE OF TRYPTOPHAN AS DEODORANT AND/OR PERFUME AGENT

CROSS REFERENCE TO RELATED APPLICATIONS

This application is a National Phase filing under 35 U.S.C. § 371 of PCT/EP2015/080696 filed on Dec. 18, 2015; and this application claims priority to Application No. 1462828 filed in France on Dec. 18, 2014 under 35 U.S.C. § 119. The entire contents of each application are hereby incorporated by reference.

This invention relates to the use of ester derivatives of tryptophan, in particular L-tryptophan as a deodorant and possibly as a perfuming agent.

This invention also relates to new ester derivatives of tryptophan, in particular L-tryptophan, as well as their methods for preparing and the compositions, the cosmetic compositions, containing them.

This invention also to a method for treating body odor, and possibly for perfuming of a human keratin material, of a textile material or of a leather article in contact with said keratin material, and in particular in the presence of sweat.

This invention further relates to the compositions, in particular cosmetic, containing at least one ester derivative of tryptophan, in particular L-tryptophan and an antiperspirant agent and/or an additional deodorant agent, as well as the use of such compositions for the treating of body odor, particularly underarm odor.

In the field of cosmetics, the use in topical application of deodorant products containing antiperspirant or deodorant type active substances for reducing or eliminating generally unpleasant body odors, in particular underarm odor, is well known.

Eccrine or apocrine sweat has a low odor when secreted. It is the degradation thereof by bacteria via enzyme reactions that produces malodorous compounds. The function of deodorant agents is that of reducing or preventing the formation of unpleasant odor. Moreover, antiperspirant substances have for effect to limit the sweat flow, and are generally constituted of aluminum salts.

Deodorant substances generally destroy the resident bacterial flora. Of these substances, the most commonly used are Triclosan (2,4,4'-trichloro-2'-hydroxydiphenylether) and farnesol which involve the drawback of modifying the ecology of skin flora significantly. There are substances that reduce bacterial growth. Of these substances, mention may be made of transition metal chelating agents such as EDTA or DPTA. These materials deprive the environment of the metals required for bacterial growth.

There is therefore a need to find novel ingredients suitable for being integrated in a cosmetic formulation for treating unpleasant body odor associated with human perspiration, particularly underarm odor.

It is common to incorporate one or more perfumes in a certain number of products or compositions, in particular cosmetic and dermatological products, with a view to mask the strong and/or unpleasant odors and/or to confer a good odor to the product or to the composition.

There is therefore a need to find novel ingredients that can both treat unpleasant body odor associated with human perspiration, particularly underarm odor, and possibly have a perfuming action.

This invention has for purpose to provide derivatives that make it possible to treat the unpleasant body odor associated with human perspiration, such as underarm odor.

One of the objects of this invention is also to provide derivatives that have a deodorant activity, in order to reduce the odors, particularly in humans, and more particularly for combating body odor, such as underarm odor.

Another object of this invention consists in providing derivatives that have both a deodorant activity, in order to reduce the odors, particularly in humans, and more particularly for combating body odor, and in particular underarm odor, and a perfuming action after application on a human keratin material, a textile material or a leather article in contact with said keratin material, and in particular in the presence of sweat.

The inventors discovered surprisingly that compounds having formula (I) detailed hereinafter, alone or in a mixture, had a good deodorant efficacy and could be readily formulated in a product intended to reduce body odor, and in particular underarm odor, alone or optionally in association with additional conventional antiperspirants and/or deodorant agents, different from the compounds of the invention, without the drawbacks mentioned above.

The compounds having formula (I) according to the invention, advantageously have a deodorant activity, making it possible to treat the unpleasant body odor associated with human perspiration, such as underarm odor.

Surprisingly, the inventors discovered that certain compounds having formula (I), in particular compounds having formulas (II) and (Ill), have both a deodorant activity and a perfuming action.

Uses

This invention relates to the use of at least one compound having formula (I) such as defined hereinafter, as a deodorant agent for treating body odor, preferably underarm odor, and possibly as a perfuming agent, typically after application on a human keratin material or after contact with a surface with a human keratin material, and in particular in the presence of sweat, particularly in a composition comprising a physiologically acceptable medium.

This invention also relates to the use of at least one compound having formula (II) such as defined hereinafter, as a perfuming agent, typically after application on a human keratin material or after contact with a surface with a human keratin material, and in particular in the presence of sweat, particularly in a composition comprising a physiologically acceptable medium.

In particular, the surface is that of a textile material or of a leather article that is able to be in contact with a keratin material, and in particular in the presence of sweat.

This invention also relates to the use of at least one compound having formula (I) combined with at least one agent antiperspirant agent and/or at least one additional deodorant agent different from the compounds having formula (I) of the invention, in particular in a cosmetic composition, for treating body odor, particularly underarm odor.

In the framework of the invention, and unless specified otherwise, the term "deodorant agent" denotes any substance that can mask, absorb, improve and/or reduce the unpleasant odor resulting from the decomposition of human sweat by bacteria.

In the framework of the invention, and unless specified otherwise, the term "antiperspirant agent" denotes a molecule that, alone, has for effect to reduce the sweat flow, reduce the damp sensation on the skin associated with human sweat and/or mask the odor of human sweat.

In the framework of the invention, and unless specified otherwise, the term "perfuming agent" denotes any substance having a pleasant odor after application, in particular after application on human keratin materials, leather articles and textile materials, preferably in contact with the human keratin materials.

In the framework of the invention, and unless specified otherwise, the term "at least one compound having formula (I)" denotes a compound having formula (I) or a mixture of different compounds having formula (I).

According to an embodiment, the compound having formula (I), (II) or (III) can be used alone or in a mixture with one or more additional antiperspirants and/or deodorant agents.

This invention also relates to a method for treating body odor, preferably underarm odor, and possibly for perfuming a human keratin material, a textile material or a leather article able to be in contact with said keratin material, and in particular in the presence of sweat, comprising a step for applying on a human keratin material, a textile material or a leather article in contact with a human keratin material, and in particular in the presence of sweat, a composition C1, C2 or C3 such as defined hereinafter.

In the framework of the invention, and unless specified otherwise, the term "human keratin material" denotes the skin, for example the skin of the face, of the body, in particular the skin of the hands, feet, underarm, scalp, and skin appendages, in particular hair. Preferably, "human keratin material" denotes the skin.

In the framework of the invention, the term "body odor" denotes for example underarm odor, plantar odor.

In the framework of the invention, "textile materials" and "leather articles" are typically those that are in contact with the human keratin materials, and in particular in the presence of sweat, such as the skin. For example, this is clothing, undergarments, socks, caps.

Among leather articles, mention can for example be made of shoes, leather clothing, watch straps, gloves.

Among textile materials, mention can for example be made of natural materials, such as cotton, linen, silk and wool, or synthetic materials such as polyamides such as nylon, polyesters, acrylics, elastanes such as Spandex® and Lycra®.

This invention also relates to a method for perfuming at least one human keratin material, at least one textile material or at least one leather article able to be in contact with said human keratin material, and in particular in the presence of sweat, comprising a step for applying on said materials, a composition C2 or C3 such as defined hereinafter.

This invention also relates to a device comprising a composition C1, C2 or C3 such as defined hereinafter, and an information notice and/or a package having visual information relating to the treatment of body odor, preferably underarm odor, and possibly visual information relating to the perfuming of a human keratin material, of a textile material or of a leather article able to be in contact with said human keratin material and in particular in the presence of sweat.

Ester Derivatives of L-Tryptophan

The ester derivatives of tryptophan according to the invention, used alone or in a mixture, are chosen from those complying with the following formula (I), along with the salts thereof, the optical and geometric isomers thereof, and the solvates thereof such as hydrates, in particular the ester derivatives of L-tryptophan, their salts, the optical and geometric isomers thereof, and the solvates thereof such as hydrates:

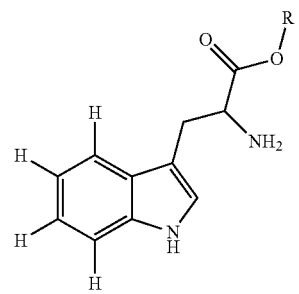

wherein R represents:
a radical —C($R_2$)($R_3$)($R_4$) wherein:
$R_2$ represents an atom of hydrogen, a ($C_1$-$C_4$) alkyl radical, linear or branched, or a ($C_1$-$C_4$) alkenyl radical, linear or branched;
$R_3$ represents an atom of hydrogen, a ($C_1$-$C_6$) alkyl radical, linear or branched, or a ($C_1$-$C_6$) alkenyl radical, linear or branched;
$R_4$ represents:
a ($C_1$-$C_{17}$) alkyl radical, linear or branched, said alkyl radical possibly substituted with at least one radical chosen in the group from: OH, (hetero) cycloalkyl comprising from 3 to 20 atoms, (hetero)cycloalkenyl comprising from 3 to 20 atoms, (hetero)aryl comprising from 5 to 20 atoms, said (hetero)cycloalkyl, (hetero)cycloalkenyl and (hetero)aryl possibly substituted with at least one radical chosen from among ($C_1$-$C_4$) alkyls, linear or branched, and ($C_1$-$C_4$) alkoxy, linear or branched;
a ($C_1$-$C_{17}$) alkenyl radical, linear or branched, said alkenyl radical possibly substituted with at least one radical chosen in the group from: OH, (hetero) cycloalkyl comprising from 3 to 20 atoms, (hetero)cycloalkenyl comprising from 3 to 20 atoms, (hetero)aryl comprising from 5 to 20 atoms, said (hetero)cycloalkyl, (hetero)cycloalkenyl and (hetero)aryl possibly substituted with at least one radical chosen from among ($C_1$-$C_4$) alkyls, linear or branched, and ($C_1$-$C_4$) alkoxy, linear or branched;
a (hetero)cycloalkyl comprising from 3 to 20 atoms, said (hetero)cycloalkyl possibly substituted with at least one radical chosen from among ($C_1$-$C_4$) alkyls, linear or branched, and ($C_1$-$C_4$) alkoxy, linear or branched;
a (hetero)aryl comprising from 5 to 20 atoms, said (hetero)aryl possibly substituted with at least one radical chosen from among: ($C_1$-$C_4$) alkyls, linear or branched, and ($C_1$-$C_4$) alkoxy, linear or branched;
a (hetero)cycloalkenyl comprising from 3 to 20 atoms, said (hetero)cycloalkenyl possibly substituted with at least one radical chosen from among: (C1-C4) alkyls, linear or branched, and (C1-C4) alkoxy, linear or branched;
a —C(O)$R_a$ radical, with $R_a$ representing a ($C_1$-$C_6$) alkyl radical, linear or branched;
$R_3$ and $R_4$ can form with the carbon atom that carries them a cycle chosen from among (hetero)cycloakyl or (hetero)cycloalkenyl comprising from 3 to 20 atoms, said (hetero)cycloalkyl and (hetero)cycloalkenyl possibly substituted with at least one radical chosen from among: $(C_1-C_4)$ alkyls, linear or branched, $(C_1-C_4)$ alkenyls, linear or branched, $(C_1-C_4)$ alkoxy, linear or branched, and (hetero)cycloalkyls comprising from 3 to 20 atoms possibly substituted with at least one $(C_1-C_4)$ alkyl radical;

a radical A chosen in the group from:
- a (hetero)aryl comprising from 5 to 20 atoms, possibly substituted with at least one radical chosen from among: $(C_1-C_4)$ alkyls, linear or branched, $(C_1-C_4)$ alkenyls, linear or branched, $(C_1-C_6)$ alcoxy, linear or branched, and (hetero)cycloalkyls comprising from 3 to 20 atoms possibly substituted with at least one $(C_1-C_6)$ alkyl radical; and
- a polycyclic radical comprising from 9 to 30 atoms, said polycyclic radical possibly substituted with at least one radical chosen from among $(C_1-C_6)$ alkyl radicals, linear or branched, and $(C_1-C_6)$ alkenyl radicals, linear or branched;

According to an embodiment, the compounds having formula (I) are chosen from among the following compounds having formula (I-1), as well as their salts, optical isomers, geometric isomers, and/or solvates:

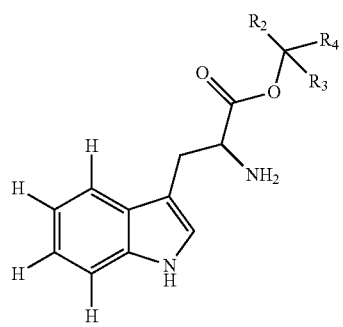

(I-1)

wherein $R_2$, $R_3$ and $R_4$ are such as defined hereinabove.

According to an embodiment, in the compounds having formula (I) or (I-1), $R_2$ and $R_3$ represent a hydrogen atom.

According to an embodiment, in the compounds having formula (I) or (I-1), $R_2$ and $R_3$ represent a hydrogen atom, and $R_4$ represents a radical chosen from among:
- a $(C_1-C_{12})$ alkyl radical, linear or branched, said alkyl radical possibly substituted with at least one radical chosen from the following group: cyclopentenyl, cyclohexenyl and phenyl, said radical possibly substituted with at least one $(C_1-C_4)$ alkyl radical such as a methyl radical, or a $(C_1-C_4)$ alkoxy radical such as a methoxy radical;
- a linear or branched $(C_1-C_{14})$ alkenyl radical;
- a (hetero)cycloalkyl comprising from 3 to 8 atoms, preferably a cycloalkyl comprising from 3 to 8 atoms such as a cyclohexan, said (hetero)cycloalkyl possibly substituted with at least one $(C_1-C_4)$ alkyl radical, linear or branched, such as an isopropyl radical;
- a (hetero)aryl comprising from 5 to 8 atoms, preferably an aryl comprising from 3 to 8 atoms such as a phenyl, said (hetero)aryl possibly substituted with at least one radical chosen from: $(C_1-C_4)$ alkyls, linear or branched such as methyl, and $(C_1-C_4)$ alkoxy, linear or branched such as methoxy.

According to an embodiment, in the compounds having formula (I) or (I-1), $R_2$ and $R_3$ represent a hydrogen atom, and $R_4$ represents in particular a radical chosen from the group comprised of the following radicals:

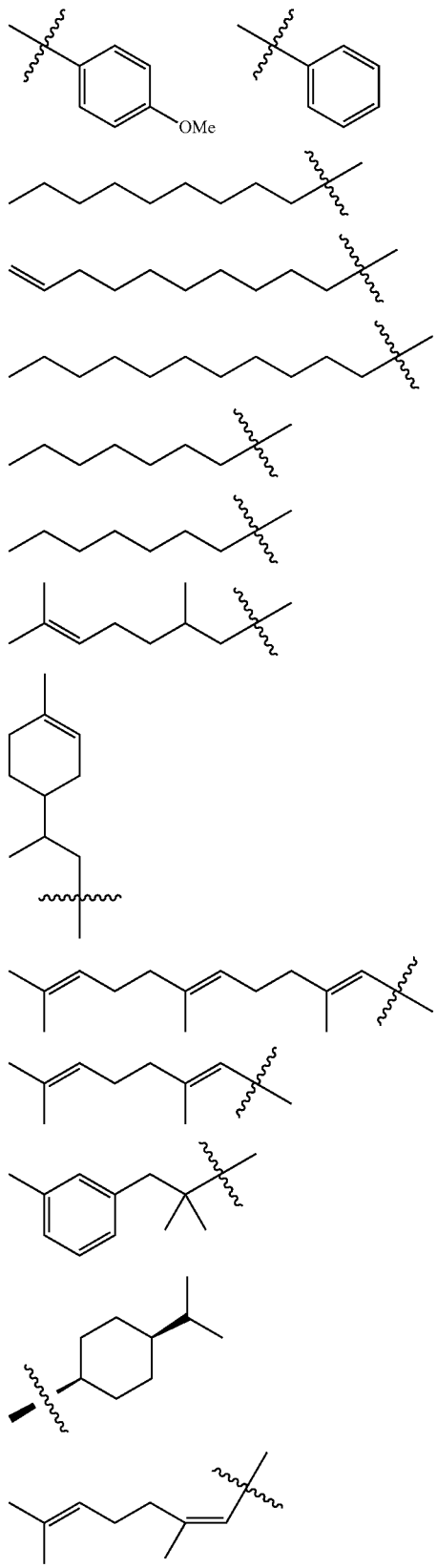

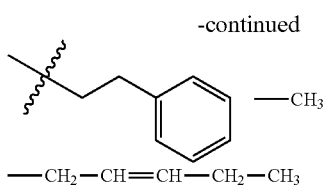

—CH₂—CH=CH—CH₂—CH₃

According to a preferred embodiment, in the compounds having formula (I) or (I-1), $R_2$ and $R_3$ represent a hydrogen atom, and $R_4$ represents a radical chosen from the group comprised of the following radicals:

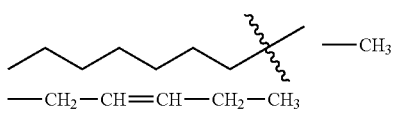

—CH₂—CH=CH—CH₂—CH₃

According to another embodiment, in the compounds having formula (I) or (I-1), $R_2$ represents a hydrogen atom and $R_3$ represents a ($C_1$-$C_6$) alkyl radical such as a methyl or pentyl radical.

According to an embodiment, in the compounds having formula (I) or (I-1), $R_2$ represents a hydrogen atom and $R_3$ represents a ($C_1$-$C_6$) alkyl radical such as a methyl or pentyl radical, and $R_4$ represents a radical chosen from:
- a ($C_1$-$C_6$) alkyl radical, linear or branched, such as a butyl radical, said alkyl radical possibly substituted with a cycloalkenyl radical comprising from 3 to 12 atoms such as cyclopentenyl, the cycloalkenyl possibly substituted with at least one radical chosen from among ($C_1$-$C_4$) alkyls, linear or branched, such as methyl;
- a ($C_1$-$C_{12}$) alkenyl radical, linear or branched, such as pentenyl, said alkenyl radical possibly substituted with a (hetero)cycloalkyl comprising from 3 to 20 atoms, said (hetero)cycloalkyl possibly substituted with at least one radical chosen from among ($C_1$-$C_4$) alkyls, linear or branched, and ($C_1$-$C_4$) alkoxy, linear or branched;
- a (hetero)cycloalkyl comprising from 3 to 20 atoms, preferably a ($C_5$-$C_8$) such as cyclohexyl said (hetero)cycloalkyl possibly substituted with at least one ($C_1$-$C_4$) alkyl radical, linear or branched, such as isopropyl;

According to an embodiment, in the compounds having formula (I) or (I-1), $R_2$ represents a hydrogen atom, $R_3$ represents a ($C_1$-$C_6$) alkyl radical such as a methyl or pentyl radical, and $R_4$ represents a radical chosen from the group comprised of the following radicals:

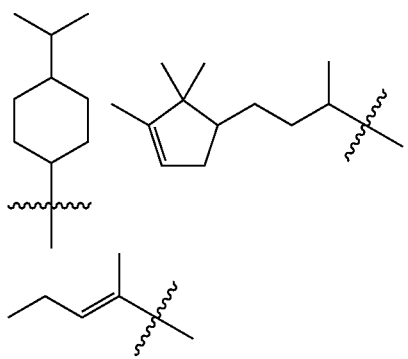

According to another embodiment, in the compounds having formula (I) or (I-1), $R_2$ and $R_3$ represent, independently of each other, a ($C_1$-$C_4$) alkyl radical, linear or branched, or a ($C_1$-$C_4$) alkenyl radical, linear or branched.

According to an embodiment, in the compounds having formula (I) or (I-1), $R_2$ and $R_3$ represent, independently of each other, a methyl, ethyl or vinyl radical, and $R_4$ is chosen from the group comprising:
- a ($C_1$-$C_{12}$) alkyl radical, linear or branched, such as a hexyl, butyl, or methyl radical, said alkyl radical possibly substituted with an aryl radical comprising from 5 to 10 atoms, such as phenyl;
- a ($C_1$-$C_{12}$) alkenyl radical, linear or branched, such as a hexenyl, heptenyl, undecenyl radical, said alkenyl radical possibly substituted with at least one radical chosen in the group comprising: OH, (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl preferably not substituted;
- a (hetero)cycloalkyl comprising from 3 to 20 atoms, such as a cycloheptan radical, said (hetero)cycloalkyl possibly substituted with at least one radical chosen from among ($C_1$-$C_4$) alkyls, linear or branched, such as methyl;
- a (hetero)cycloalkenyl comprising from 3 to 20 atoms, such as a cyclohexenyl radical, said (hetero)cycloalkenyl possibly substituted with at least one ($C_1$-$C_4$) alkyl radical, linear or branched, such as methyl.

According to an embodiment, in the compounds having formula (I) or (I-1), —C($R_2$)($R_3$)($R_4$), preferably represents a radical chosen from:

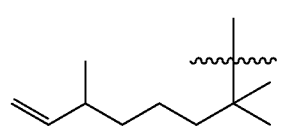

(p)

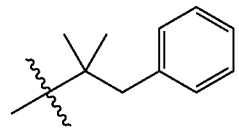

(q)

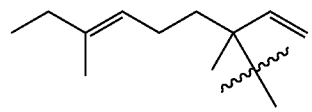

(d)

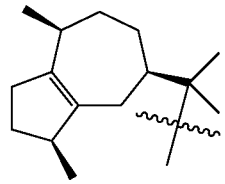

(v)

-continued

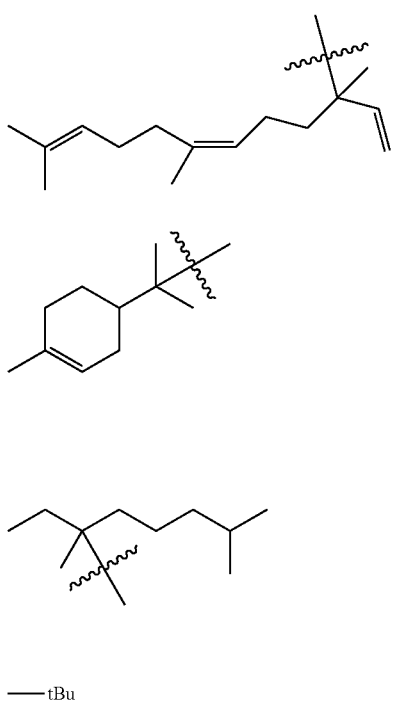

(ab)

(af)

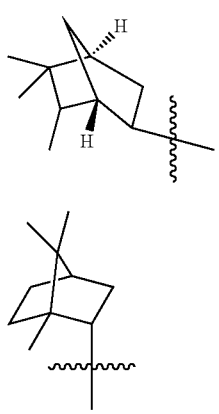

——tBu (ah)

According to another embodiment, in the compounds having formula (I) or (I-1), $R_2$ represents a hydrogen atom or a ($C_1$-$C_4$) alkyl radical such as a methyl or isopropyl radical, and $R_3$ and $R_4$ form together with the carbon atom that carries them a cycle chosen from (hetero)cycloakyl or (hetero)cycloalkenyl comprising from 3 to 20 atoms, said cycle possibly substituted with at least one radical chosen from among: ($C_1$-$C_4$) alkyls, linear or branched, ($C_1$-$C_4$) alkenyls, linear or branched, ($C_1$-$C_4$) alkoxy, linear or branched, and (hetero)cycloalkyls comprising from 3 to 20 atoms possibly substituted with at least one ($C_1$-$C_4$) alkyl radical.

According to an embodiment, in the compounds having formula (I) or (I-1), —C($R_2$)($R_3$)($R_4$), represents in particular a radical chosen from the group constituted of the following radicals:

-continued

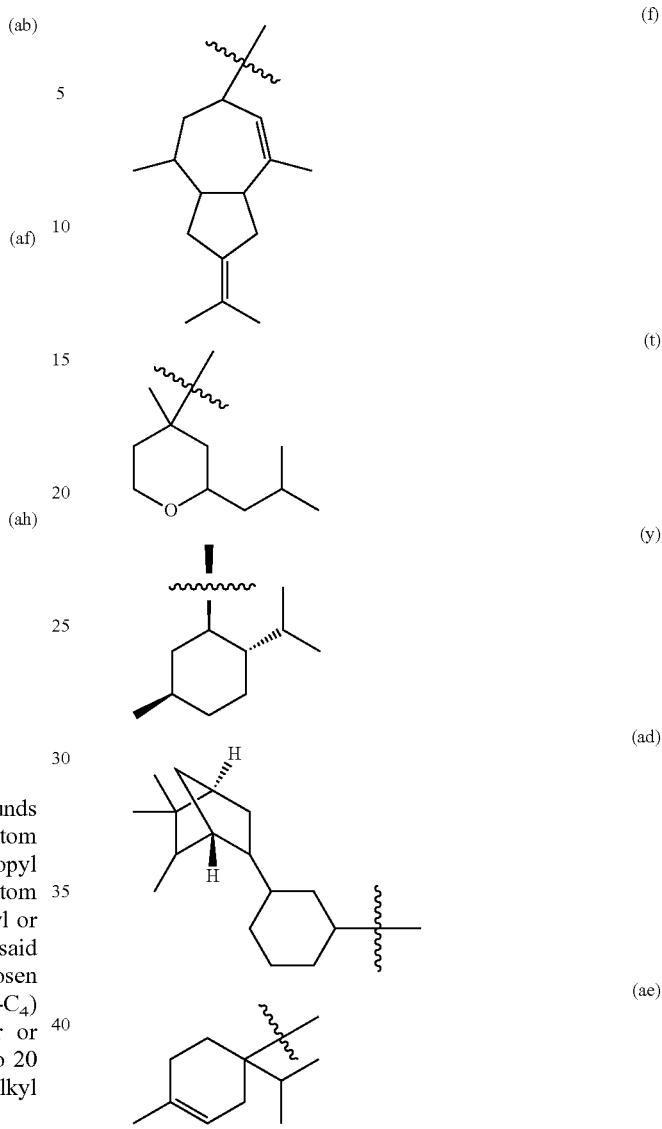

(f)

(t)

(y)

(ad)

(ae)

According to an embodiment, the compounds having formula (I) are chosen from among the following compounds having formula (I-2), as well as their salts, optical isomers, geometric isomers, and/or solvates:

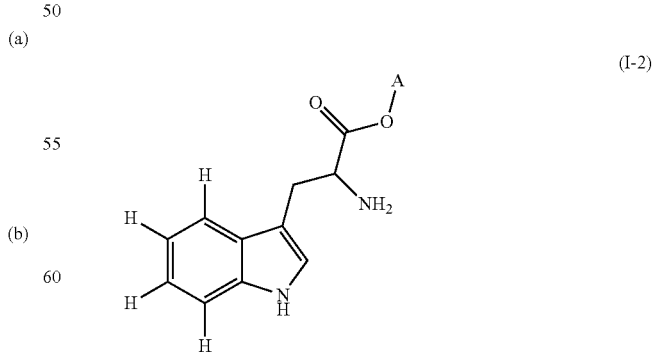

(I-2)

wherein A is such as defined hereinabove.

According to an embodiment, in the compounds having formula (I) or (I-2), A represents a (hetero)aryl radical comprising from 5 to 20 atoms, preferably an aryl radical such as phenyl, said (hetero)aryl radical possibly substituted with at least one radical chosen from among: $(C_1-C_4)$ alkyls, linear or branched, $(C_1-C_4)$ alkenyls, linear or branched, preferably by a $(C_1-C_4)$ alkenyl, linear or branched, such as propenyl.

According to a preferred embodiment, in the compounds having formula (I) or (I-2), A preferably represents the following radical:

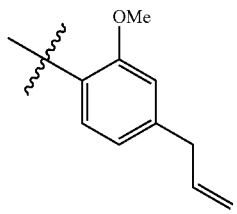

(r)

According to another embodiment, in the compounds having formula (I) or (I-2), A represents a polycyclic radical comprising from 9 to 30 atoms, said polycyclic radical possibly substituted with at least one radical chosen from among the group comprised of $(C_1-C_6)$ alkyl radicals, linear or branched, and $(C_1-C_6)$ alkenyl radicals, linear or branched.

According to a preferred embodiment, A represents one of the following radicals:

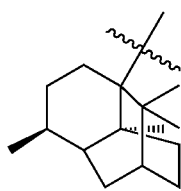

(e)

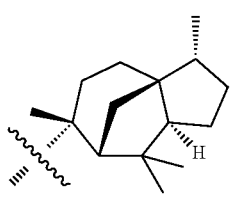

(c)

According to a preferred embodiment, the compounds having formula (I), as well as their salts, optical isomers, geometric isomers, and/or solvates, are such that R represents a radical chosen from one of the following radicals:

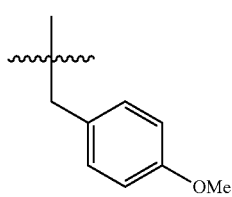

(g)

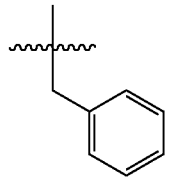

(h)

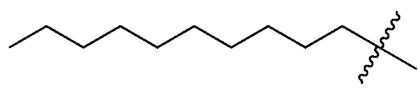

(i)

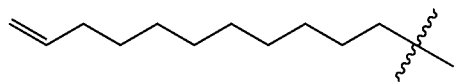

(j)

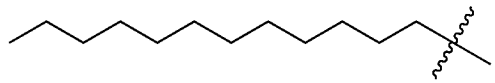

(k)

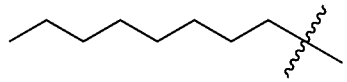

(l)

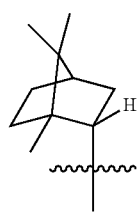

(b)

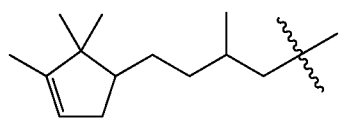

(m)

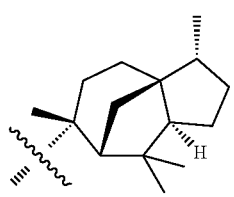

(c)

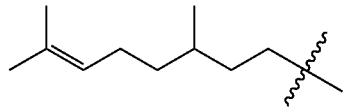

(n)

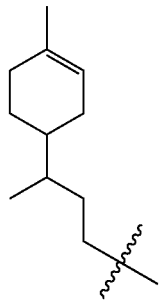

(o)

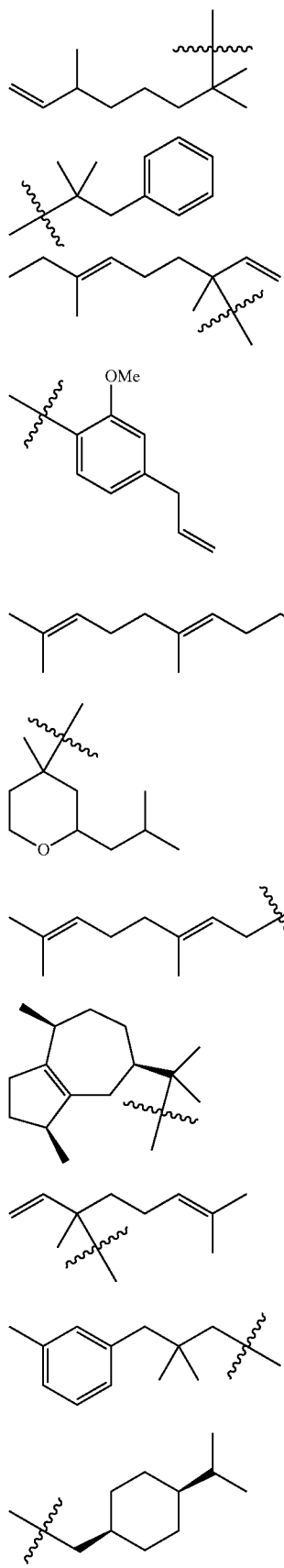
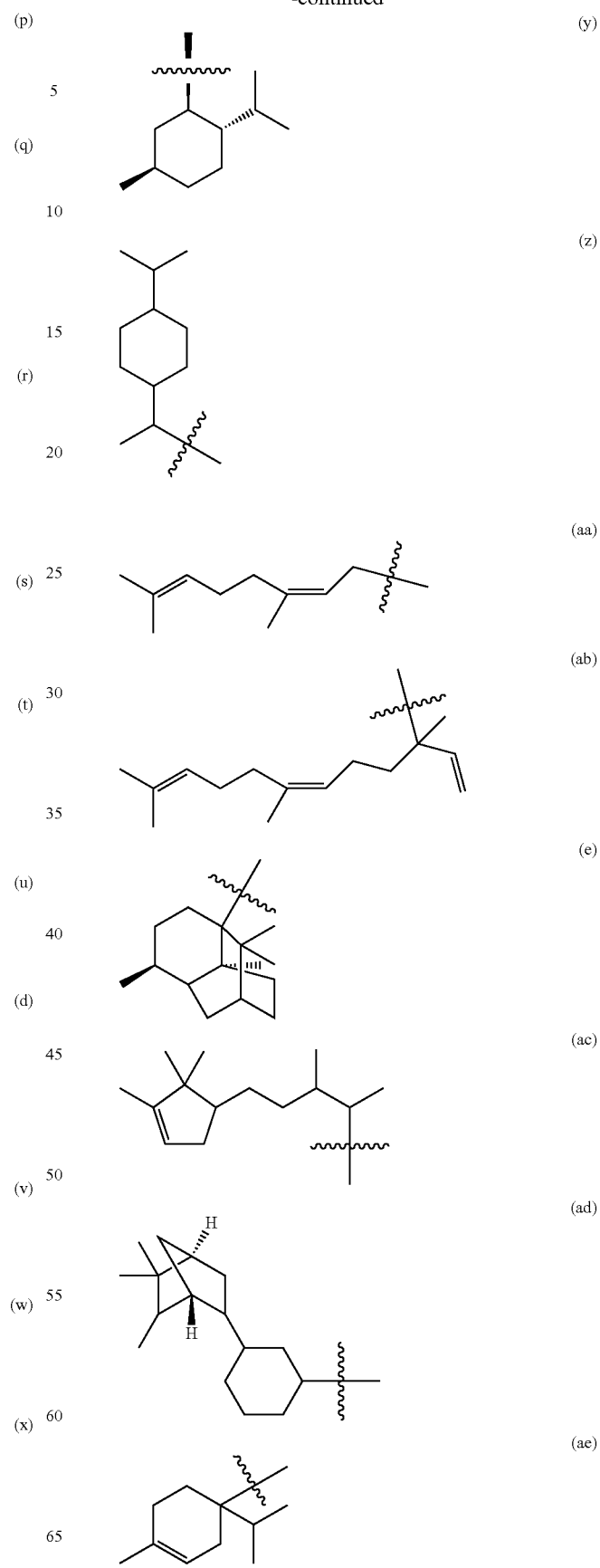

-continued

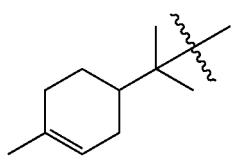

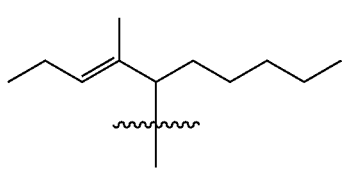

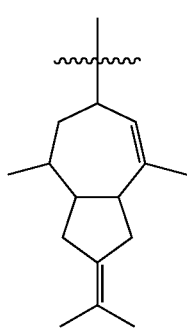

—CH₂—CH₃

—CH₂—CH₂—CH=CH—CH₂—CH₃
—tBu

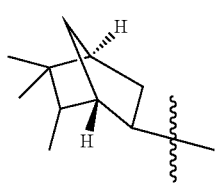

In particular, among the compounds having formula (I), mention can be made for example of the following preferred compounds:

Tryptophan ethyl ester hydrochloride of the following structure:

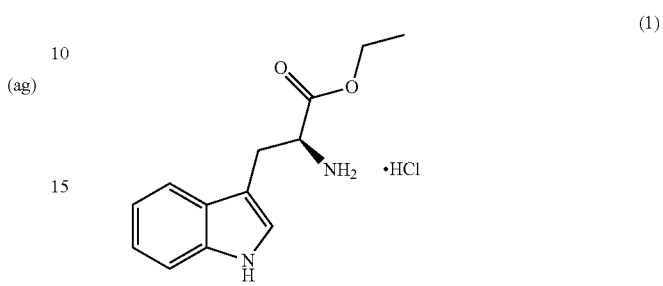

(1)

Tryptophan cis-3-hexenyl ester of the following structure:

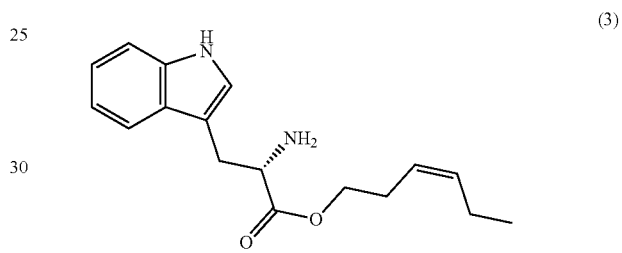

(3)

Tryptophan cis-3-hexenyl ester hydrochloride of the following structure:

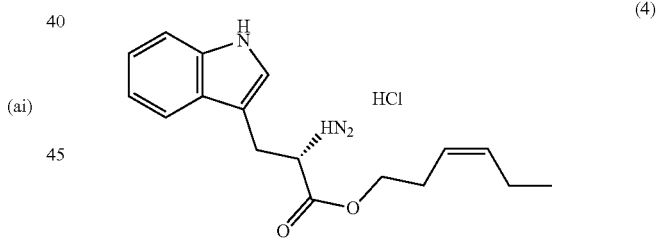

(4)

Tryptophan dihydromyrcenyl ester of structure:

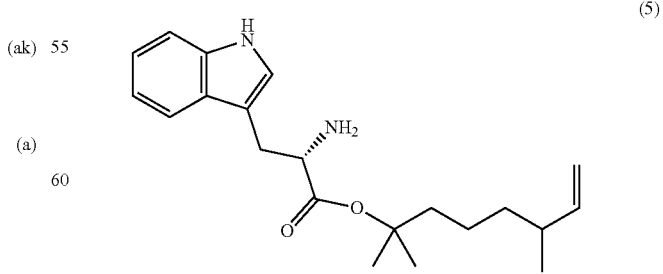

(5)

Tryptophan octyl ester hydrochloride of the following structure:

(6)

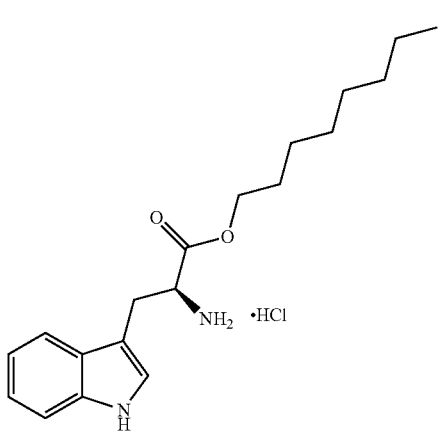

Tryptophan benzyl ester of structure:

(7)

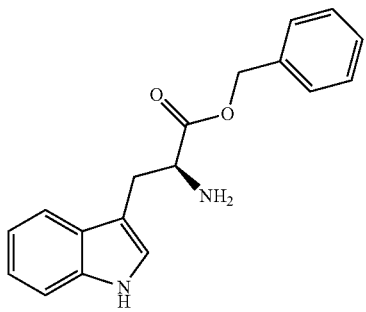

Tryptophan tertiobutyl ester hydrochloride of the following structure:

(8)

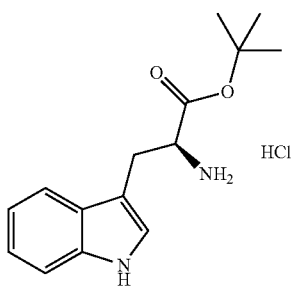

Among the aforementioned compounds having formula (I) used according to the invention, certain compounds have, in addition to their deodorant activity, a perfuming activity after contact with a keratin material and in particular in the presence of sweat.

These are in particular the following compounds having formula (II) as well as their salts, optical isomers, geometric isomers, and/or solvates:

(II)

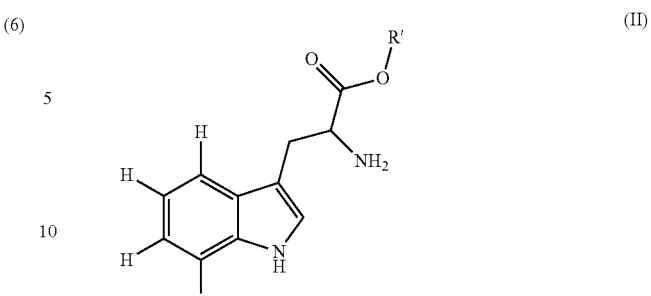

wherein R' represents:
a radical —C(R'$_2$)(R'$_3$)(R'$_4$) wherein:
R'$_2$ represents an atom of hydrogen, a (C$_1$-C$_4$) alkyl radical, linear or branched, or a (C$_1$-C$_4$) alkenyl radical, linear or branched;
R'$_3$ represents an atom of hydrogen, a (C$_1$-C$_6$) alkyl radical, linear or branched, or a (C$_1$-C$_6$) alkenyl radical, linear or branched;
R'$_4$ represents:
a (C$_1$-C$_{17}$), preferably (C$_5$-C$_{17}$) alkyl radical, linear or branched, said alkyl radical possibly substituted with at least one radical chosen in the group from: OH, a (hetero)cycloalkyl comprising from 3 to 20 atoms, a (hetero)cycloalkenyl comprising from 3 to 20 atoms, a (hetero)aryl comprising from 5 to 20 atoms, said (hetero)cycloalkyl, (hetero)cycloalkenyl and (hetero)aryl possibly substituted with at least one radical chosen from among (C$_1$-C$_4$) alkyls, linear or branched, and (C$_1$-C$_4$) alkoxy, linear or branched;
a (C$_3$-C$_{17}$), preferably (C$_5$-C$_{17}$) alkenyl radical, linear or branched, said alkenyl radical possibly substituted with at least one radical chosen in the group from: OH, (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among (C$_1$-C$_4$) alkyls, linear or branched, and (C$_1$-C$_4$) alkoxy, linear or branched;
a (hetero)cycloalkyl comprising from 3 to 20 atoms, said (hetero)cycloalkyl possibly substituted with at least one radical chosen from among (C$_1$-C$_4$) alkyls, linear or branched, and (C$_1$-C$_4$) alkoxy, linear or branched;
a (hetero)aryl comprising from 5 to 20 atoms, said (hetero)aryl possibly substituted with at least one radical chosen from among (C$_1$-C$_4$) alkyls, linear or branched, and (C$_1$-C$_4$) alkoxy, linear or branched;
a (hetero)cycloalkenyl comprising from 5 to 20 atoms, said (hetero)cycloalkenyl possibly substituted with at least one radical chosen from among (C$_1$-C$_4$) alkyls, linear or branched, and (C$_1$-C$_4$) alkoxy, linear or branched;
a —C(O)R$_a$ radical, with R$_a$ representing a (C$_1$-C$_6$) alkyl radical;
R'$_3$ and R'$_4$ can form with the carbon atom that carries them a cycle chosen from among (hetero)cycloakyl or (hetero)cycloalkenyl comprising from 3 to 20 atoms, said cycle possibly substituted with at least one radical chosen from among: ($C_1$-$C_4$) alkyls, linear or branched, ($C_1$-$C_4$) alkenyls, linear or branched, ($C_1$-$C_4$) alkoxy, linear or branched, and (hetero)cycloalkyls comprising from 3 to 20 atoms possibly substituted with at least one ($C_1$-$C_4$) alkyl radical;

a radical A' chosen in the group from:
  a (hetero)aryl comprising from 5 to 20 atoms, possibly substituted with at least one radical chosen from among: ($C_1$-$C_4$) alkyls, linear or branched, ($C_1$-$C_4$) alkenyls, linear or branched, ($C_1$-$C_6$) alkoxy, linear or branched, and (hetero)cycloalkyls comprising from 3 to 20 atoms possibly substituted with at least one ($C_1$-$C_6$) alkyl radical; and
  a polycyclic radical comprising from 9 to 30 atoms, said polycyclic radical possibly substituted with at least one radical chosen from among the group comprising: ($C_1$-$C_4$) alkyls, linear or branched, and ($C_1$-$C_6$) alkenyls, linear or branched;

provided that when $R'_2$ and $R'_3$ represent a hydrogen atom, $R'_4$ does not represent a ($C_1$-$C_2$) alkyl radical, According to the invention, the compounds having formula (II) are a sub-family of the compounds having formula (I).

According to an embodiment, the compounds having formula (II) are chosen from among the following compounds having formula (II-1), as well as their salts, optical isomers, geometric isomers, and/or solvates:

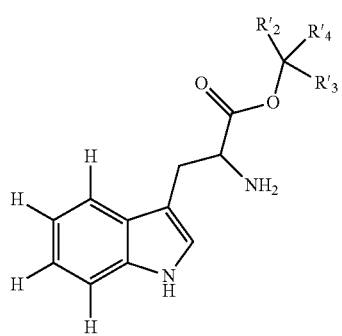

(II-1)

wherein $R'_2$, $R'_3$ and $R'_4$ are such as defined hereinabove.

According to an embodiment, in the compounds having formula (II) or (II-1), $R'_2$ and $R'_3$ represent a hydrogen atom.

According to an embodiment, in the compounds having formula (II) or (II-1), $R'_2$ and $R'_3$ represent a hydrogen atom, and $R'_4$ represents a radical chosen from among:
  a ($C_3$-$C_{17}$) alkyl radical, linear or branched, said alkyl radical possibly substituted with a radical chosen in the group from: cyclopentenyl, cyclohexenyl and phenyl, said radical possibly substituted with at least one ($C_1$-$C_4$) alkyl radical such as a methyl radical, or a ($C_1$-$C_4$) alkoxy radical such as a methoxy radical;
  a ($C_1$-$C_2$) alkyl radical substituted with a (hetero)aryl comprising from 5 to 20 atoms, said (hetero)aryl possibly substituted with a methoxy radical;
  a linear or branched ($C_3$-$C_{17}$) alkenyl radical;
  a (hetero)cycloalkyl comprising from 3 to 8 atoms, preferably a cycloalkyl comprising from 3 to 8 atoms such as a cyclohexan, said (hetero)cycloalkyl possibly substituted with at least one ($C_1$-$C_4$) alkyl radical, linear or branched, such as an isopropyl radical;
  a (hetero)aryl comprising from 5 to 8 atoms, preferably an aryl comprising from 3 to 8 atoms such as a phenyl, said (hetero)aryl possibly substituted with at least one radical chosen from: ($C_1$-$C_4$) alkyls, linear or branched such as methyl, and ($C_1$-$C_4$) alkoxy, linear or branched such as methoxy.

According to an embodiment, in the compounds having formula (II) or (II-1), $R'_2$ and $R'_3$ represent a hydrogen atom, and $R'_4$ represents a radical chosen from the group comprised of the following radicals:

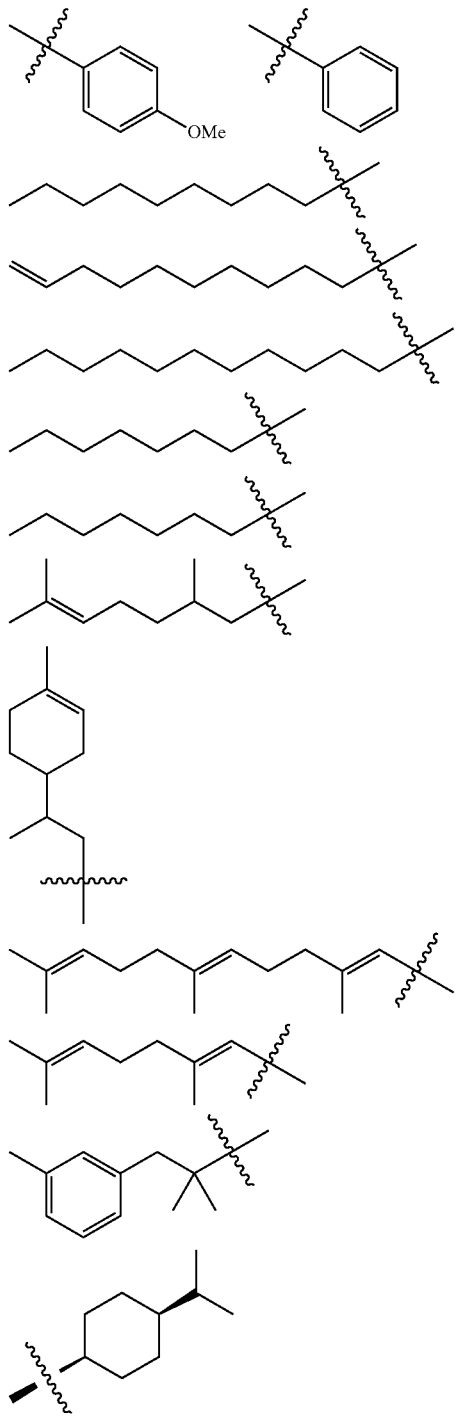

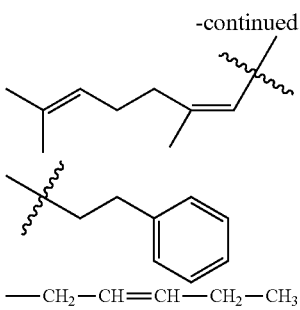

—CH$_2$—CH=CH—CH$_2$—CH$_3$

According to a preferred embodiment, in the compounds having formula (II) or (II-1), R'$_2$ and R'$_3$ represent a hydrogen atom, and R'$_4$ represents in particular a radical chosen from the group comprised of the following radicals:

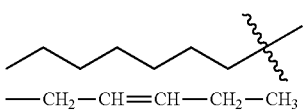

—CH$_2$—CH=CH—CH$_2$—CH$_3$

According to another embodiment, in the compounds having formula (II) or (II-1), R'$_2$ represents a hydrogen atom and R'$_3$ represents a (C$_1$-C$_6$) alkyl radical such as a methyl or pentyl radical.

According to an embodiment, in the compounds having formula (II) or (II-1), R'$_2$ represents a hydrogen atom and R'$_3$ represents a (C$_1$-C$_6$) alkyl radical such as a methyl or pentyl radical, and R'$_4$ preferably represents a radical chosen from:
- a (C$_3$-C$_6$) alkyl radical, linear or branched, such as a butyl radical, said alkyl radical possibly substituted with a cycloalkenyl radical comprising from 3 to 12 atoms such as cyclopentenyl, the cycloalkenyl possibly substituted with at least one radical chosen from among (C$_1$-C$_4$) alkyls, linear or branched, such as methyl;
- a (C$_3$-C$_{12}$) alkenyl radical, linear or branched, such as pentenyl, said alkenyl radical possibly substituted with a (hetero)cycloalkyl comprising from 3 to 20 atoms, said (hetero)cycloalkyl possibly substituted with at least one radical chosen from among (C$_1$-C$_4$) alkyls, linear or branched, and (C$_1$-C$_4$) alkoxy, linear or branched;
- a (hetero)cycloalkyl comprising from 3 to 20 atoms, preferably a (C$_5$-C$_8$) such as cyclohexyl said (hetero)cycloalkyl possibly substituted with a (C$_1$-C$_4$) alkyl radical, linear or branched, such as isopropyl.

According to an embodiment, in the compounds having formula (II) or (II-1), R'$_2$ represents a hydrogen atom, R'$_3$ represents a (C$_1$-C$_6$) alkyl radical such as a methyl or pentyl radical, and R'$_4$ in particular represents a radical chosen from the group comprised of the following radicals:

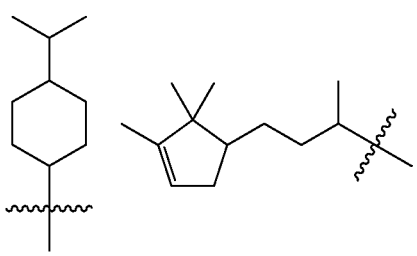

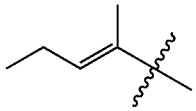

According to another embodiment, in the compounds having formula (II) or (II-1), R'$_2$ and R'$_3$ represent, independently of each other, a (C$_1$-C$_4$) alkyl radical, linear or branched, or a (C$_1$-C$_4$) alkenyl radical, linear or branched.

According to an embodiment, in the compounds having formula (II) or (II-1), R'$_2$ and R'$_3$ represent, independently of each other, a methyl, ethyl or vinyl radical, and R'$_4$ is chosen from the group comprising:
- a (C$_1$-C$_{12}$), preferably (C$_3$-C$_{12}$) alkyl radical, linear or branched, such as a hexyl, butyl, or methyl radical, said alkyl radical possibly substituted with an aryl radical comprising from 5 to 10 atoms, such as phenyl;
- a (C$_3$-C$_{12}$) alkenyl radical, linear or branched, such as a hexenyl, heptenyl, undecenyl radical, said alkenyl radical possibly substituted with at least one radical chosen in the group comprising: OH, (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl preferably not substituted;
- a (hetero)cycloalkyl comprising from 3 to 20 atoms, such as a cycloheptan radical, said (hetero)cycloalkyl possibly substituted with at least one radical chosen from among (C$_1$-C$_4$) alkyls, linear or branched, such as methyl;
- a (hetero)cycloalkenyl comprising from 3 to 20 atoms, such as a cyclohexenyl radical, said (hetero)cycloalkenyl possibly substituted with at least one (C$_1$-C$_4$) alkyl radical, linear or branched, such as methyl.

According to an embodiment, in the compounds having formula (II) or (II-1), —C(R'$_2$)(R'$_3$)(R'$_4$), preferably represents a radical chosen from:

(p)

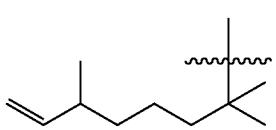

(q)

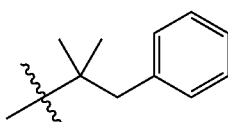

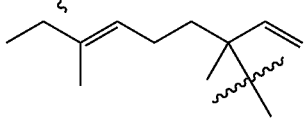

(d)

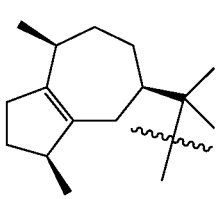

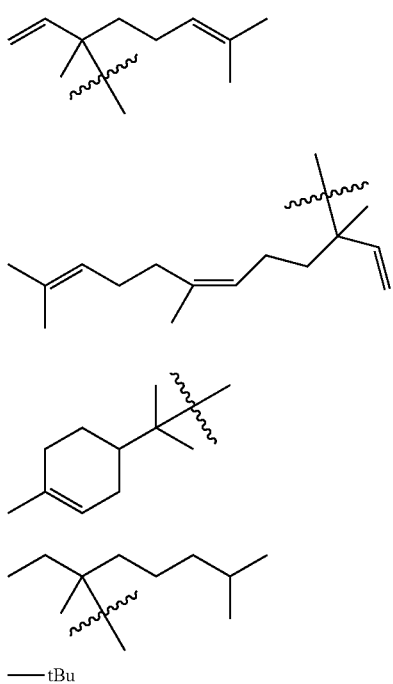

According to another embodiment, in the compounds having formula (II) or (II-1), $R'_2$ represents a hydrogen atom or a $(C_1-C_4)$ alkyl radical such as a methyl or isopropyl radical, and $R'_3$ and $R'_4$ form together with the carbon atom that carries them a cycle chosen from (hetero)cycloakyl or (hetero)cycloalkenyl comprising from 3 to 20 atoms, said cycle possibly substituted with at least one radical chosen from among: $(C_1-C_4)$ alkyls, linear or branched, $(C_1-C_4)$ alkenyls, linear or branched, $(C_1-C_4)$ alkoxy, linear or branched, and (hetero)cycloalkyls comprising from 3 to 20 atoms possibly substituted with at least one $(C_1-C_4)$ alkyl radical.

According to an embodiment, in the compounds having formula (II) or (II-1), —C($R'_2$)($R'_3$)($R'_4$), represents in particular a radical chosen from the group constituted of the following radicals:

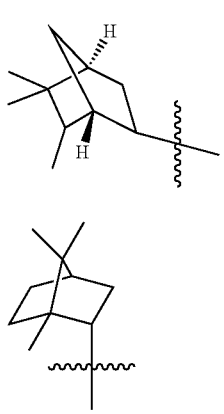

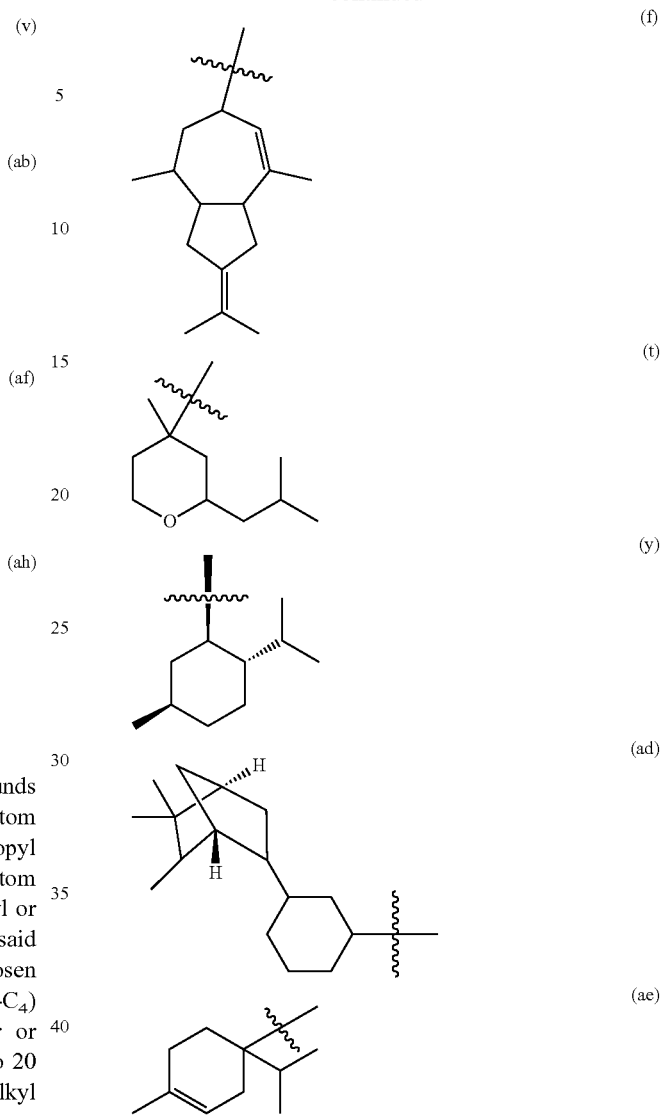

According to an embodiment, the compounds having formula (II) are chosen from among the following compounds having formula (II-2), as well as their salts, optical isomers, geometric isomers, and/or solvates:

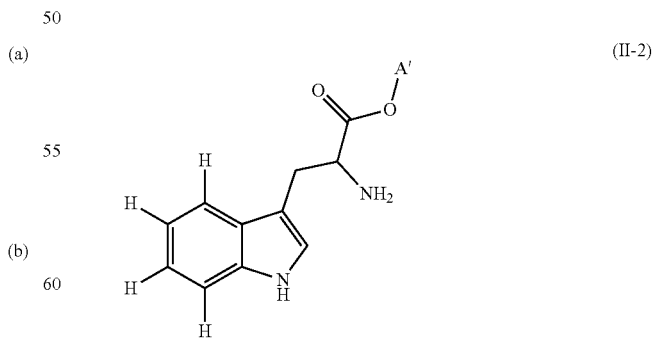

wherein A' is such as defined hereinabove.

According to an embodiment, in the compounds having formula (II) or (II-2), A' represents a (hetero)aryl radical comprising from 5 to 20 atoms, preferably an aryl radical such as phenyl, said (hetero)aryl radical possibly substituted with at least one radical chosen from among: ($C_1$-$C_4$) alkyls, linear or branched, ($C_1$-$C_4$) alkenyls, linear or branched, preferably by a ($C_1$-$C_4$) alkenyl, linear or branched, such as propenyl.

According to a preferred embodiment, in the compounds having formula (II) or (II-2), A' preferably represents the following radical:

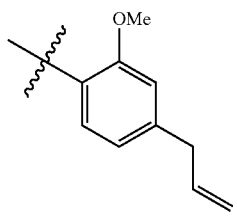 (r)

According to another embodiment, in the compounds having formula (II) or (II-2), A' represents a polycyclic radical comprising from 9 to 30 atoms, said polycyclic radical possibly substituted with at least one radical chosen from among the group comprised of ($C_1$-$C_6$) alkyl radicals, linear or branched, and ($C_1$-$C_6$) alkenyl radicals, linear or branched.

According to a preferred embodiment, A' represents one of the following radicals:

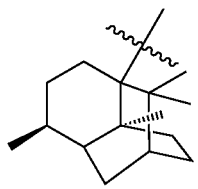 (e)

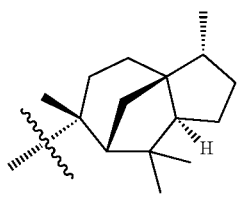 (c)

According to a preferred embodiment, the compounds having formula (II), as well as their salts, optical isomers, geometric isomers, and/or solvates, are such that R' represents a radical chosen from one of the following radicals:

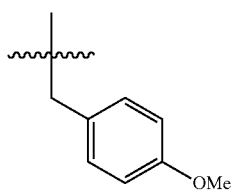 (g)

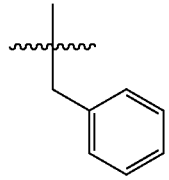 (h)

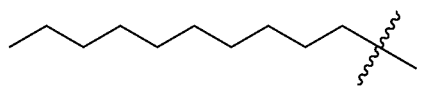 (i)

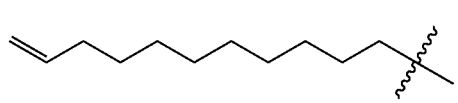 (j)

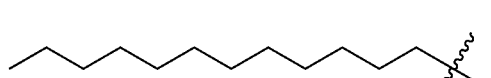 (k)

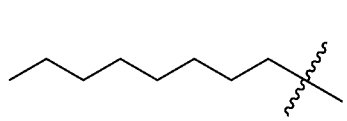 (l)

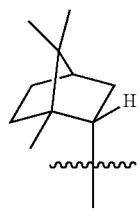 (b)

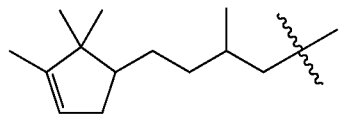 (m)

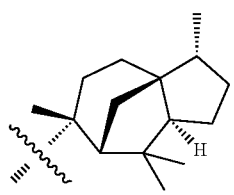 (c)

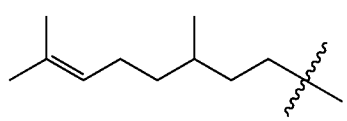 (n)

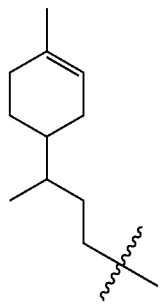 (o)

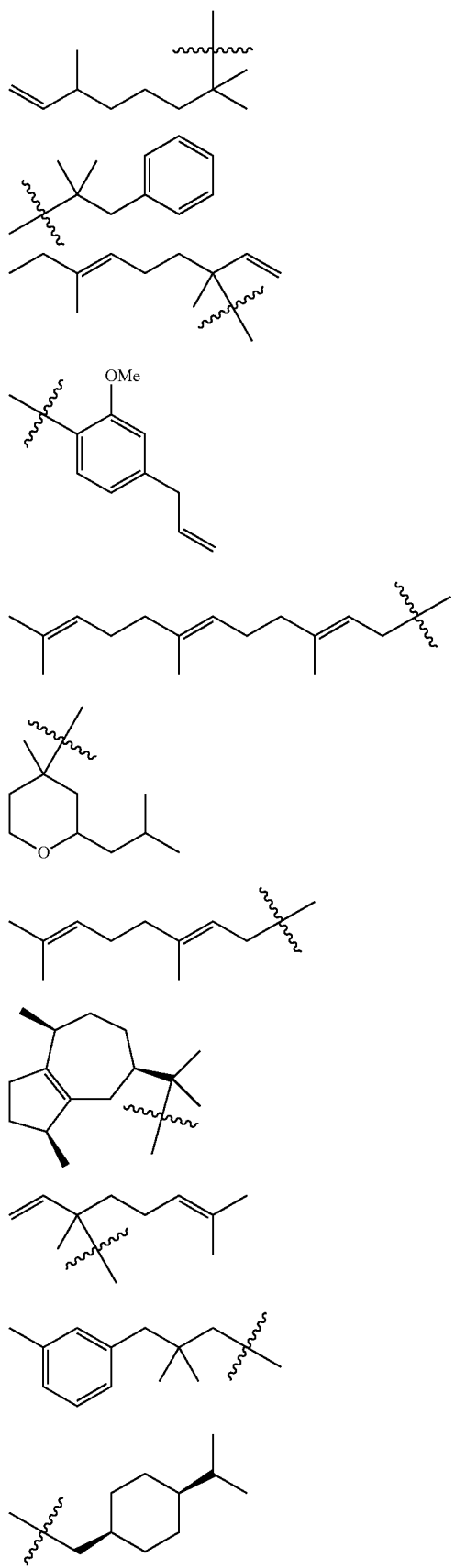
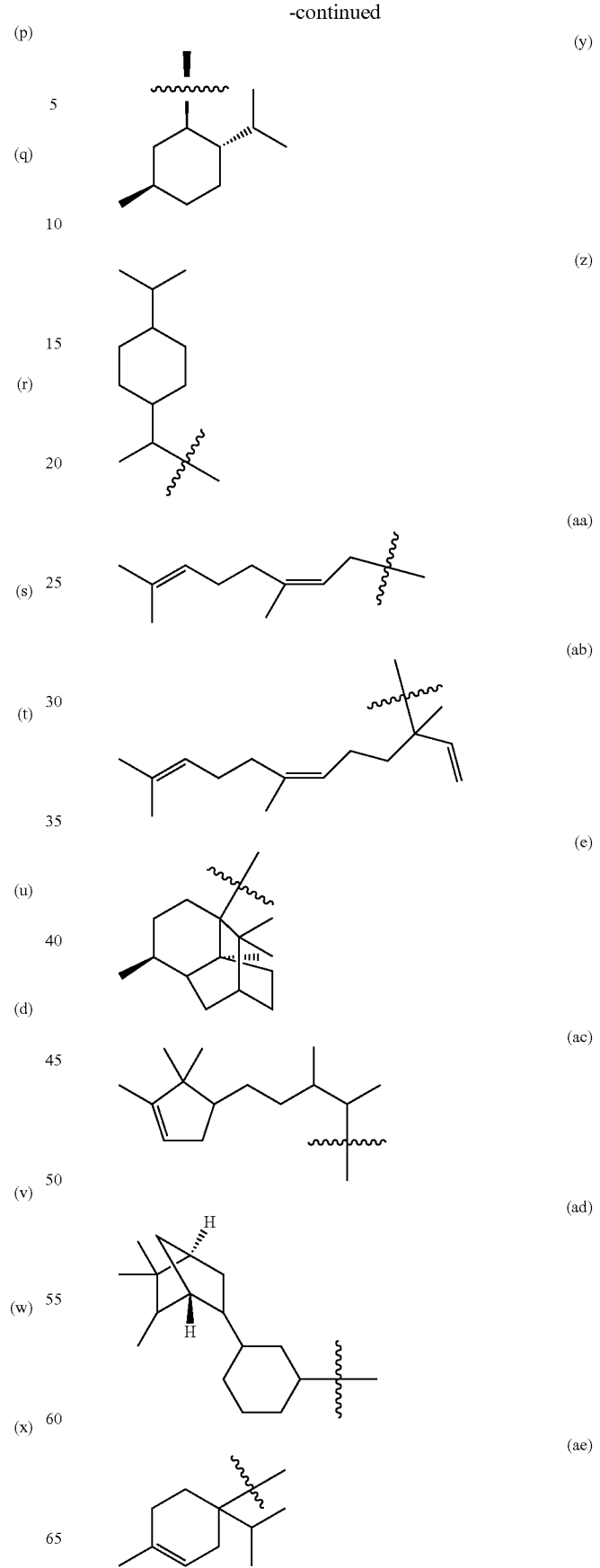

-continued

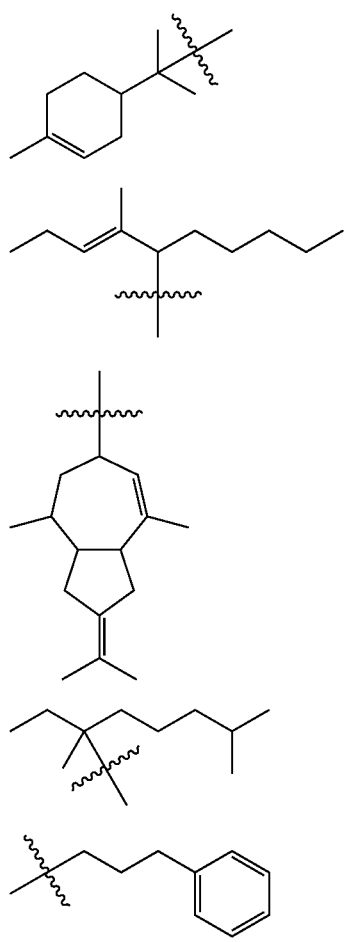

(af)

(ag)

(f)

(ah)

(ai)

(ak)

—CH$_2$—CH$_2$—CH═CH—CH$_2$—CH$_3$ (a)

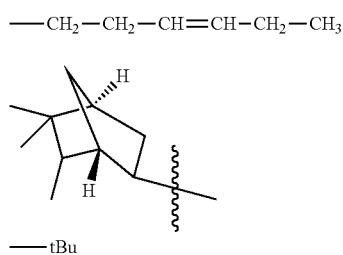

—tBu

In particular, among the preferred compounds having formula (II), mention can be made for example of the following preferred compounds:

Tryptophan cis-3-hexenyl ester of the following structure:

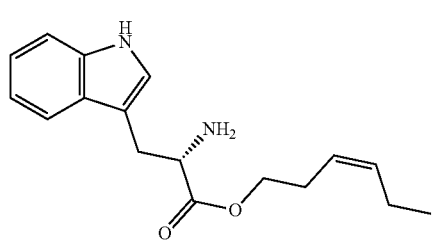
(3)

Tryptophan cis-3-hexenyl ester hydrochloride of the following structure:

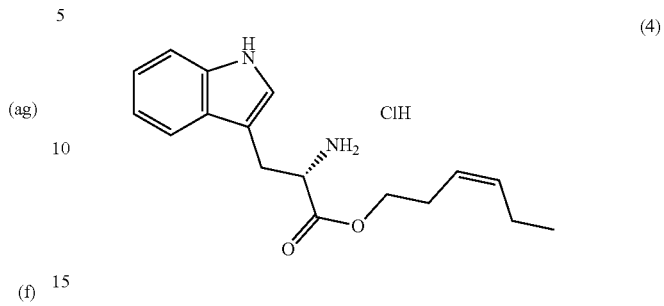
(4)

Tryptophan dihydromyrcenyl ester of the following structure:

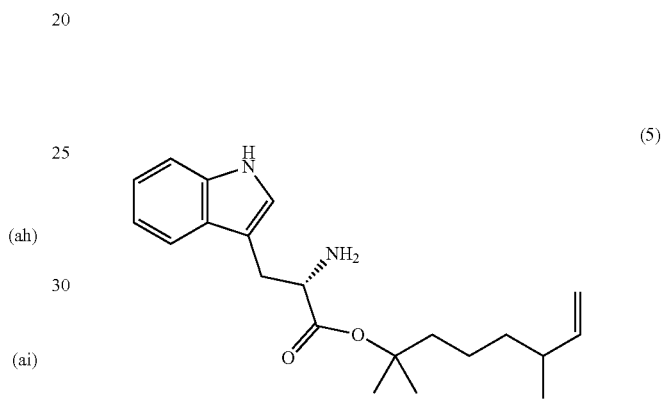
(5)

Tryptophan octyl ester hydrochloride of the following structure:

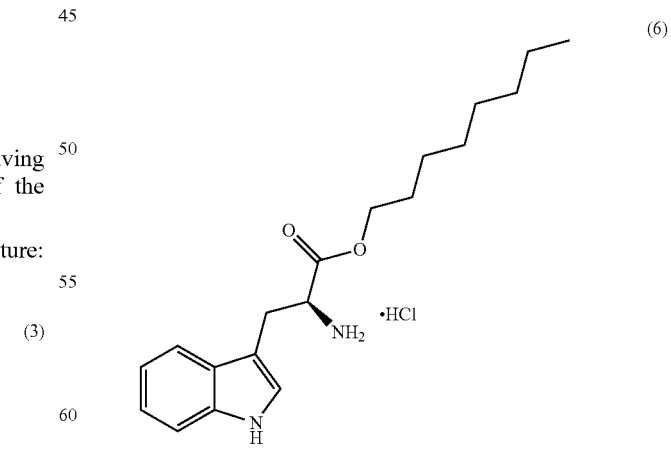
(6)

Tryptophan tertiobutyl ester hydrochloride of the following structure:

(8)

[Structure: tert-butyl ester of tryptophan, HCl salt]

Among the compounds having formula (I), and in particular among those having formula (II), certain compounds are new as such constitute an object of the invention.

This invention also relates to compounds having the following formula (III):

(III)

[Structure: tryptophan ester with OR" group]

wherein R" represents:
- a radical —C(R"$_2$)(R"$_3$)(R"$_4$) wherein:
  R"$_2$ represents a (C$_1$-C$_4$) alkyl radical, linear or branched, or a (C$_1$-C$_4$) alkenyl radical, linear or branched;
  R"$_3$ represents a hydrogen atom, a (C$_1$-C$_6$) alkyl radical, linear or branched, or a (C$_1$-C$_6$) alkenyl radical, linear or branched;
  R"$_4$ represents:
  - a (C$_1$-C$_{17}$) alkyl radical, linear or branched, said alkyl radical possibly substituted with at least one radical chosen in the group from: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among (C$_1$-C$_4$) alkyls, linear or branched, and (C$_1$-C$_4$) alkoxy, linear or branched;
  - a (C$_3$-C$_{17}$) alkenyl radical, linear or branched, said alkenyl radical possibly substituted with at least one radical chosen in the group from: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among (C$_1$-C$_4$) alkyls, linear or branched, and (C$_1$-C$_4$) alkoxy, linear or branched;
  - a (hetero)cycloalkyl comprising from 3 to 20 atoms, said (hetero)cycloalkyl possibly substituted with at least one radical chosen from among (C$_1$-C$_4$) alkyls, linear or branched, and (C$_1$-C$_4$) alkoxy, linear or branched;
  - a (hetero)aryl comprising from 5 to 20 atoms, said (hetero)aryl possibly substituted with at least one radical chosen from among (C$_1$-C$_4$) alkyls, linear or branched, and (C$_1$-C$_4$) alkoxy, linear or branched;
  - a (hetero)cycloalkenyl comprising from 3 to 20 atoms, said (hetero)cycloalkenyl possibly substituted with at least one radical chosen from among (C$_1$-C$_4$) alkyls, linear or branched, and (C$_1$-C$_4$) alkoxy, linear or branched;
  R"$_3$ and R"$_4$ can form with the carbon atom that carries them a cycle chosen from among (hetero)cycloakyl or (hetero)cycloalkenyl comprising from 3 to 20 atoms, said cycle possibly substituted with at least one radical chosen from among: (C$_1$-C$_4$) alkyls, linear or branched, (C$_1$-C$_4$) alkenyls, linear or branched, (C$_1$-C$_4$) alkoxy, linear or branched, and (hetero)cycloalkyls comprising from 3 to 20 atoms possibly substituted with at least one (C$_1$-C$_4$) alkyl radical;
- a radical —CH$_2$—R"$_5$ wherein R"$_5$ represents:
  - a (C$_2$-C$_{17}$) alkenyl radical, linear or branched, said alkenyl radical possibly substituted with at least one radical chosen in the group comprising: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among (C$_1$-C$_4$) alkyls, linear or branched or (C$_1$-C$_4$) alkoxy, linear or branched;
  - a (C$_2$-C$_{17}$) alkyl radical, linear or branched, substituted with at least one radical chosen in the group comprising: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among (C$_1$-C$_4$) alkyls, linear or branched or (C$_1$-C$_4$) alkoxy, linear or branched;
  - a (hetero)cycloalkyl comprising from 3 to 20 atoms, said (hetero)cycloalkyl possibly substituted with at least one radical chosen from among (C$_1$-C$_4$) alkyls, linear or branched, and (C$_1$-C$_4$) alkoxy, linear or branched;
  - a (hetero)cycloalkenyl comprising from 3 to 20 atoms, said (hetero)cycloalkenyl possibly substituted with at least one radical chosen from among (C$_1$-C$_4$) alkyls, linear or branched, and (C$_1$-C$_4$) alkoxy, linear or branched;
- a radical A" chosen in the group from:
  - a (hetero)aryl comprising from 5 to 20 atoms, possibly substituted with at least one radical chosen from among: (C$_1$-C$_4$) alkyls, linear or branched, (C$_1$-C$_4$) alkenyls, linear or branched, (C$_1$-C$_6$) alkoxy, linear or branched, and (hetero)cycloalkyls comprising from 3 to 20 atoms possibly substituted with at least one (C$_1$-C$_6$) alkyl radical; and
  - a polycyclic radical comprising from 9 to 30 atoms, said polycyclic radical possibly substituted with at least one radical chosen from among the group comprising: (C$_1$-C$_6$) alkyl radicals, linear or branched, and (C$_1$-C$_6$) alkenyl radicals, linear or branched;

and provided that:

R″ does not represent —CH(CH$_3$)—C$_2$H$_5$ or —(CH$_2$)$_7$—CH=CH—(CH$_2$)$_7$—CH$_3$; or when A″ represents a (hetero)cycloalkyl, A″ does not represent one of the following radicals:

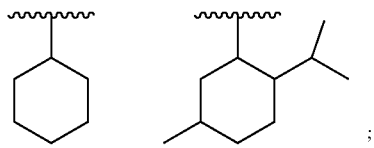 [SMILES: *C1CCCCC1 ; *C1CC(C)CCC1C(C)C]

as well as their salts, optical isomers, geometric isomers, and/or solvates.

According to an embodiment, the compounds having formula (III) according to the invention are not one of the following compounds, nor their salts:

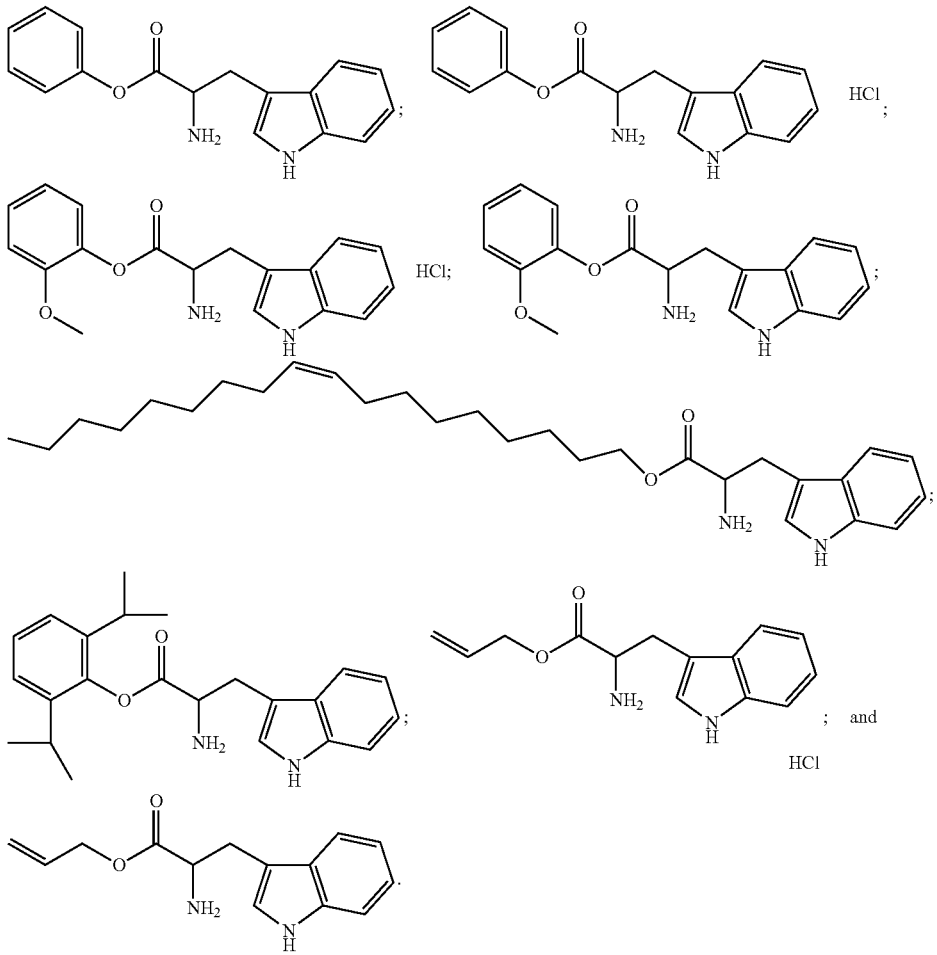

According to an embodiment, the aforementioned compounds having formula (III) do not comply with the following compound:

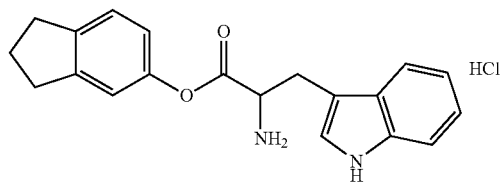

According to an embodiment, this invention relates to compounds having formula (III) wherein R″ represents:

a radical —C(R″$_2$)(R″$_3$)(R″$_4$) wherein:

R″$_2$ represents a (C$_1$-C$_4$) alkyl radical, linear or branched, or a (C$_1$-C$_4$) alkenyl radical, linear or branched;

R″$_3$ represents a hydrogen atom, a (C$_1$-C$_6$) alkyl radical, linear or branched, or a (C$_1$-C$_6$) alkenyl radical, linear or branched;

R″$_4$ represents:

a (C$_1$-C$_{17}$) alkyl radical, linear or branched, said alkyl radical possibly substituted with at least one radical chosen in the group from: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among ($C_1$-$C_4$) alkyls, linear or branched, and ($C_1$-$C_4$) alkoxy, linear or branched;
a ($C_3$-$C_{17}$) alkenyl radical, linear or branched, said alkenyl radical possibly substituted with at least one radical chosen in the group from: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among ($C_1$-$C_4$) alkyls, linear or branched, and ($C_1$-$C_4$) alkoxy, linear or branched;
a (hetero)cycloalkyl comprising from 3 to 20 atoms, said (hetero)cycloalkyl possibly substituted with at least one radical chosen from among ($C_1$-$C_4$) alkyls, linear or branched, and ($C_1$-$C_4$) alkoxy, linear or branched;
a (hetero)aryl comprising from 5 to 20 atoms, said (hetero)aryl possibly substituted with at least one radical chosen from among ($C_1$-$C_4$) alkyls, linear or branched, and ($C_1$-$C_4$) alkoxy, linear or branched;
a (hetero)cycloalkenyl comprising from 3 to 20 atoms, said (hetero)cycloalkenyl possibly substituted with at least one radical chosen from among ($C_1$-$C_4$) alkyls, linear or branched, and ($C_1$-$C_4$) alkoxy, linear or branched;
$R''_3$ and $R''_4$ can form with the carbon atom that carries them a cycle chosen from among (hetero)cycloakyl or (hetero)cycloalkenyl comprising from 3 to 20 atoms, said cycle possibly substituted with at least one radical chosen from among: ($C_1$-$C_4$) alkyls, linear or branched, ($C_1$-$C_4$) alkenyls, linear or branched, ($C_1$-$C_4$) alkoxy, linear or branched, and (hetero)cycloalkyls comprising from 3 to 20 atoms possibly substituted with at least one ($C_1$-$C_4$) alkyl radical;
a radical —$CH_2$—$R''_5$ wherein $R''_5$ represents:
a ($C_3$-$C_{17}$), preferably ($C_3$-$C_{16}$), more preferably ($C_5$-$C_{15}$), and in particular ($C_5$-$C_9$) alkenyl radical, linear or branched, said alkenyl radical possibly substituted with at least one radical chosen in the group comprising: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among ($C_1$-$C_4$) alkyls, linear or branched or ($C_1$-$C_4$) alkoxy, linear or branched;
a ($C_2$-$C_{17}$) alkyl radical, linear or branched, substituted with at least one radical chosen in the group comprising: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among ($C_1$-$C_4$) alkyls, linear or branched or ($C_1$-$C_4$) alkoxy, linear or branched;
a (hetero)cycloalkyl comprising from 3 to 20 atoms, said (hetero)cycloalkyl possibly substituted with at least one radical chosen from among ($C_1$-$C_4$) alkyls, linear or branched, and ($C_1$-$C_4$) alkoxy, linear or branched;
a (hetero)cycloalkyl comprising from 3 to 20 atoms, said (hetero)cycloalkenyl possibly substituted with at least one radical chosen from among ($C_1$-$C_4$) alkyls, linear or branched, and ($C_1$-$C_4$) alkoxy, linear or branched;
a radical A" chosen in the group from:
a heteroaryl comprising from 5 to 20 atoms, possibly substituted with at least one radical chosen from among: ($C_1$-$C_4$) alkyls, linear or branched, ($C_1$-$C_4$) alkenyls, linear or branched, ($C_1$-$C_6$) alcoxy, linear or branched, and (hetero)cycloalkyls comprising from 3 to 20 atoms possibly substituted with at least one ($C_1$-$C_6$) alkyl radical;
an aryl comprising from 5 to 20 atoms, possibly substituted with at least one radical chosen from among: ($C_1$-$C_4$) alkyls, linear or branched, ($C_1$-$C_4$) alkenyls, linear or branched, ($C_1$-$C_6$) alkoxy, linear or branched, and (hetero)cycloalkyls comprising from 3 to 20 atoms possibly substituted with at least one ($C_1$-$C_6$) alkyl radical; and
a polycyclic radical comprising from 9 to 30 atoms, preferably from 10 to 30 atoms, said polycyclic radical possibly substituted with at least one radical chosen from among the group comprising: ($C_1$-$C_6$) alkyl radicals, linear or branched, and ($C_1$-$C_6$) alkenyl radicals, linear or branched;
and provided that:
R" does not represent —$CH(CH_3)$—$C_2H_5$, —$(CH_2)_7$—$CH$=$CH$—$(CH_2)_7$—$CH_3$, or —$(CH_2)_8$—$CH$=$CH$—$(CH_2)_7$—$CH_3$; or
A" does not represent one of the following radicals:

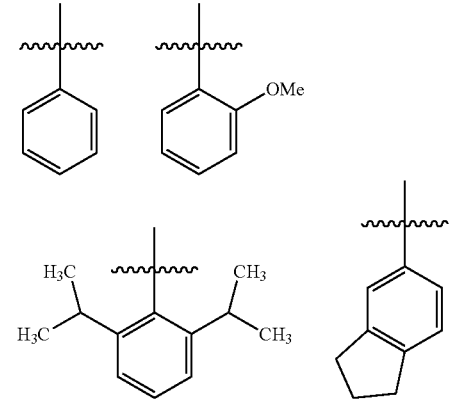

as well as their salts, optical isomers, geometric isomers, and/or solvates.

According to the invention, when R" does not represent —$(CH_2)_8$—$CH$=$CH$—$(CH_2)_7$—$CH_3$, it corresponds to the fact that $R''_5$ does not represent —$(CH_2)_7$—$CH$=$CH$—$(CH_2)_7$—$CH_3$.

According to an embodiment, this invention relates to compounds having formula (III) wherein R" represents:
a radical —$C(R''_2)(R''_3)(R''_4)$ wherein:
$R''_2$ represents a ($C_1$-$C_4$) alkyl radical, linear or branched, or a ($C_1$-$C_4$) alkenyl radical, linear or branched;
$R''_3$ represents a hydrogen atom, a ($C_1$-$C_6$) alkyl radical, linear or branched, or a ($C_1$-$C_6$) alkenyl radical, linear or branched;
$R''_4$ represents:
a ($C_1$-$C_{17}$) alkyl radical, linear or branched, said alkyl radical possibly substituted with at least one radical chosen in the group from: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among $(C_1-C_4)$ alkyls, linear or branched, and $(C_1-C_4)$ alkoxy, linear or branched;

a $(C_3-C_{17})$ alkenyl radical, linear or branched, said alkenyl radical possibly substituted with at least one radical chosen in the group from: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among $(C_1-C_4)$ alkyls, linear or branched, and $(C_1-C_4)$ alkoxy, linear or branched;

a (hetero)cycloalkyl comprising from 3 to 20 atoms, said (hetero)cycloalkyl possibly substituted with at least one radical chosen from among $(C_1-C_4)$ alkyls, linear or branched, and $(C_1-C_4)$ alkoxy, linear or branched;

a (hetero)aryl comprising from 5 to 20 atoms, said (hetero)aryl possibly substituted with at least one radical chosen from among $(C_1-C_4)$ alkyls, linear or branched, and $(C_1-C_4)$ alkoxy, linear or branched;

a (hetero)cycloalkenyl comprising from 3 to 20 atoms, said (hetero)cycloalkenyl possibly substituted with at least one radical chosen from among $(C_1-C_4)$ alkyls, linear or branched, and $(C_1-C_4)$ alkoxy, linear or branched;

$R''_3$ and $R''_4$ can form with the carbon atom that carries them a cycle chosen from among (hetero)cycloakyl or (hetero)cycloalkenyl comprising from 3 to 20 atoms, said cycle possibly substituted with at least one radical chosen from among: $(C_1-C_4)$ alkyls, linear or branched, $(C_1-C_4)$ alkenyls, linear or branched, $(C_1-C_4)$ alkoxy, linear or branched, and (hetero)cycloalkyls comprising from 3 to 20 atoms possibly substituted with at least one $(C_1-C_4)$ alkyl radical;

a radical $-CH_2-R''_5$ wherein $R''_5$ represents:

a $(C_3-C_{17})$, preferably $(C_3-C_{16})$, more preferably $(C_5-C_{15})$, and in particular $(C_5-C_9)$ alkenyl radical, linear or branched, said alkenyl radical possibly substituted with at least one radical chosen in the group comprising: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among $(C_1-C_4)$ alkyls, linear or branched or $(C_1-C_4)$ alkoxy, linear or branched;

a $(C_2-C_{17})$ alkyl radical, linear or branched, substituted with at least one radical chosen in the group comprising: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl possibly substituted with at least one radical chosen from among $(C_1-C_4)$ alkyls, linear or branched or $(C_1-C_4)$ alkoxy, linear or branched;

a (hetero)cycloalkyl comprising from 3 to 20 atoms, said (hetero)cycloalkyl possibly substituted with at least one radical chosen from among $(C_1-C_4)$ alkyls, linear or branched, and $(C_1-C_4)$ alkoxy, linear or branched;

a (hetero)cycloalkenyl comprising from 3 to 20 atoms, said (hetero)cycloalkenyl possibly substituted with at least one radical chosen from among $(C_1-C_4)$ alkyls, linear or branched, and $(C_1-C_4)$ alkoxy, linear or branched;

a radical A" chosen in the group from:

a heteroaryl comprising from 5 to 20 atoms, possibly substituted with at least one radical chosen from among: $(C_1-C_4)$ alkyls, linear or branched, $(C_1-C_4)$ alkenyls, linear or branched, $(C_1-C_6)$ alcoxy, linear or branched, and (hetero)cycloalkyls comprising from 3 to 20 atoms possibly substituted with at least one $(C_1-C_6)$ alkyl radical;

an aryl comprising from 5 to 20 atoms with the exception of phenyl, possibly substituted with at least one radical chosen from among: $(C_1-C_4)$ alkyls, linear or branched, $(C_1-C_4)$ alkenyls, linear or branched, $(C_1-C_6)$ alkoxy, linear or branched, and (hetero)cycloalkyls comprising from 3 to 20 atoms possibly substituted with at least one $(C_1-C_6)$ alkyl radical; and a polycyclic radical comprising from 9 to 30 atoms with the exception of indane, preferably from 10 to 30 atoms, said polycyclic radical possibly substituted with at least one radical chosen from among the group comprising: $(C_1-C_6)$ alkyl radicals, linear or branched, and $(C_1-C_6)$ alkenyl radicals, linear or branched;

and provided that:

R" does not represent $-CH(CH_3)-C_2H_5$, or $-(CH_2)_8-CH=CH-(CH_2)_7-CH_3$; as well as their salts, optical isomers, geometric isomers, and/or solvates.

According to an embodiment, the compounds having formula (III) are chosen from among the following compounds having formula (III-1), as well as their salts, optical isomers, geometric isomers, and/or solvates:

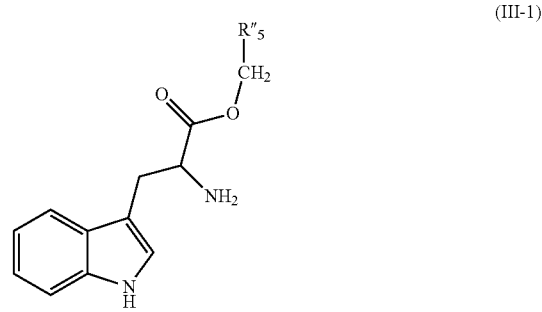

(III-1)

wherein $R''_5$ is such as defined hereinabove.

According to an embodiment, the compounds having formula (III) are chosen from among the following compounds having formula (III-1), as well as their salts, optical isomers, geometric isomers, and/or solvates:

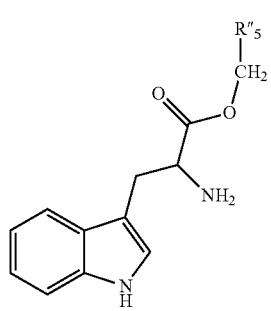

(III-1)

wherein R″₅ is such as defined hereinabove, provided that R″₅ does not represent —(CH₂)₇—CH═CH—(CH₂)₇—CH₃ or —CH═CH₂.

According to an embodiment, in the compounds having formula (III) or (III-1), R″₅ represents a radical chosen from among:
- a ($C_3$-$C_{17}$) alkyl radical, linear or branched, substituted with a radical chosen in the group from: cyclopentenyl, cyclohexenyl and phenyl, said radical possibly substituted with at least one ($C_1$-$C_4$) alkyl radical such as a methyl radical, or a ($C_1$-$C_4$) alkoxy radical such as a methoxy radical;
- a linear or branched ($C_3$-$C_{17}$) alkenyl radical;
- a (hetero)cycloalkyl comprising from 3 to 8 atoms, preferably a cycloalkyl comprising from 3 to 8 atoms such as a cyclohexan, said (hetero)cycloalkyl possibly substituted with at least one ($C_1$-$C_4$) alkyl radical, linear or branched, such as an isopropyl radical.

According to an embodiment, in the compounds having formula (III) or (III-1), R″₅ represents a radical chosen from among:
- a ($C_3$-$C_{17}$) alkyl radical, linear or branched, substituted with a radical chosen in the group from: cyclopentenyl, cyclohexenyl and phenyl, said radical possibly substituted with at least one ($C_1$-$C_4$) alkyl radical such as a methyl radical, or a ($C_1$-$C_4$) alkoxy radical such as a methoxy radical;
- a ($C_3$-$C_{16}$), preferably ($C_5$-$C_{15}$), and in particular ($C_5$-$C_9$) alkenyl radical, linear or branched;
- a (hetero)cycloalkyl comprising from 3 to 8 atoms, preferably a cycloalkyl comprising from 3 to 8 atoms such as a cyclohexan, said (hetero)cycloalkyl possibly substituted with at least one ($C_1$-$C_4$) alkyl radical, linear or branched, such as an isopropyl radical;

provided that R″₅ does not represent —(CH₂)₇—CH═CH—(CH₂)₇—CH₃.

According to an embodiment, in the compounds having formula (III) or (III-1), R″₅ represents a radical chosen from among:
- a ($C_3$-$C_{17}$) alkyl radical, linear or branched, substituted with a radical chosen in the group from: cyclopentenyl, cyclohexenyl and phenyl, said radical possibly substituted with at least one ($C_1$-$C_4$) alkyl radical such as a methyl radical, or a ($C_1$-$C_4$) alkoxy radical such as a methoxy radical;
- a ($C_3$-$C_{16}$), preferably ($C_5$-$C_{15}$), and in particular ($C_5$-$C_9$) alkenyl radical, linear or branched;
- a (hetero)cycloalkyl comprising from 3 to 8 atoms, preferably a cycloalkyl comprising from 3 to 8 atoms such as a cyclohexan, said (hetero)cycloalkyl possibly substituted with at least one ($C_1$-$C_4$) alkyl radical, linear or branched, such as an isopropyl radical.

According to an embodiment, in the compounds having formula (III) or (III-1), R″₅ represents a ($C_3$-$C_{16}$), preferably ($C_5$-$C_{15}$), and in particular ($C_5$-$C_9$) alkenyl radical, linear or branched.

According to an embodiment, in the compounds having formula (III) or (III-1), R″₅ represents a radical chosen from the group comprising the following radicals:

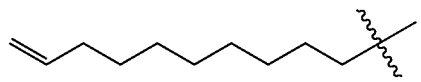
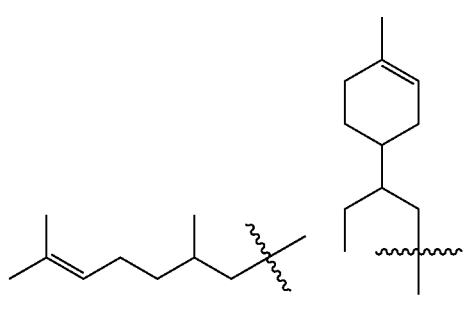
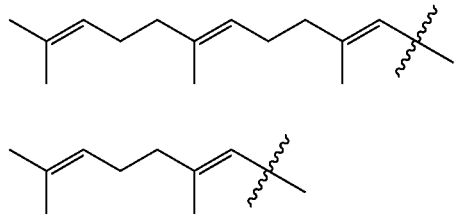
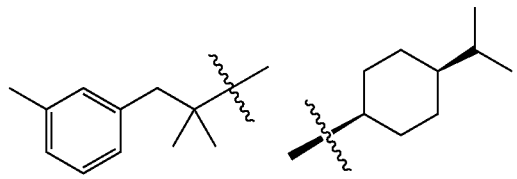
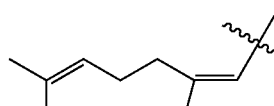
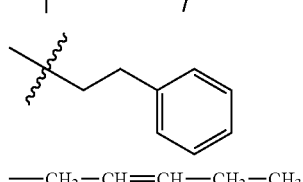

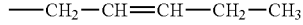

According to a preferred embodiment, in the compounds having formula (III) or (III-1), R″₅ in particular represents the following radical:

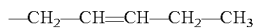

According to an embodiment, the compounds having formula (III) are chosen from among the following compounds having formula (III-2), as well as their salts, optical isomers, geometric isomers, and/or solvates:

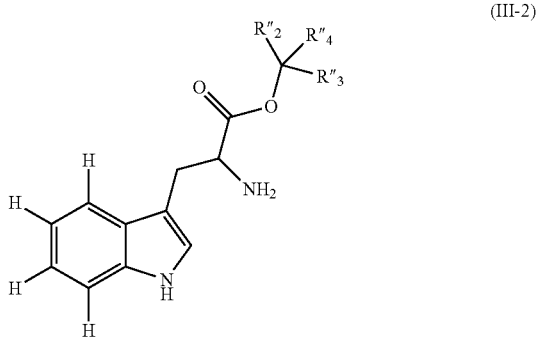
(III-2)

wherein R″₂, R″₃ and R″₄ are such as defined hereinabove.

According to an embodiment, in the compounds having formula (III) or (III-2), R″₃ represents a hydrogen atom and R″₂ represents a (C₁-C₄) alkyl radical such as a methyl radical.

According to an embodiment, in the compounds having formula (III) or (III-2), R″₃ represents a hydrogen atom, R″₂ represents a (C₁-C₄) alkyl radical such as a methyl radical, and R″₄ preferably represents a radical chosen from:
- a (C₃-C₆) alkyl radical, linear or branched, such as a butyl radical, said alkyl radical possibly substituted with a cycloalkenyl radical comprising from 3 to 12 atoms such as cyclopentenyl, the cycloalkenyl possibly substituted with at least one radical chosen from among (C₁-C₄) alkyls, linear or branched, such as methyl;
- a (C₃-C₁₂) alkenyl radical, linear or branched, such as pentenyl, said alkenyl radical possibly substituted with a (hetero)cycloalkyl comprising from 3 to 20 atoms, said (hetero)cycloalkyl possibly substituted with at least one radical chosen from among (C₁-C₄) alkyls, linear or branched, and (C₁-C₄) alkoxy, linear or branched;
- a (hetero)cycloalkyl comprising from 3 to 20 atoms, preferably a (C₅-C₈) such as cyclohexyl said (hetero)cycloalkyl possibly substituted with a (C₁-C₄) alkyl radical, linear or branched, such as isopropyl.

According to an embodiment, in the compounds having formula (III) or (III-2), R″₃ represents a hydrogen atom, R″₂ represents a (C₁-C₄) alkyl radical such as a methyl radical, and R″₄ in particular represents a radical chosen from the group comprised of the following radicals:

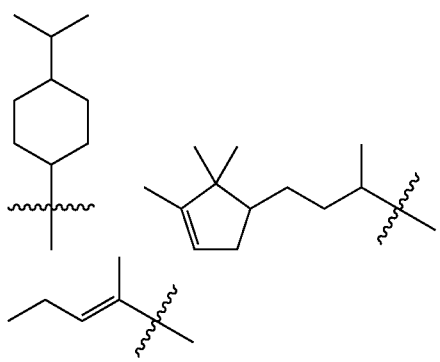

According to another embodiment, in the compounds having formula (III) or (III-2), R″₂ and R″₃ represent, independently of each other, a (C₁-C₄) alkyl radical, linear or branched, or a (C₂-C₄) alkenyl radical, linear or branched.

According to an embodiment, in the compounds having formula (III) or (III-2), R″₂ and R″₃ represent, independently of each other, a methyl, ethyl or vinyl radical, and R″₄ is chosen from the group comprising:
- a (C₃-C₁₂) alkyl radical, linear or branched, such as a hexyl or butyl radical, said alkyl radical possibly substituted with an aryl radical comprising from 5 to 10 atoms, such as phenyl;
- a (C₃-C₁₂) alkenyl radical, linear or branched, such as a hexenyl, heptenyl, undecenyl radical, said alkenyl radical possibly substituted with at least one radical chosen in the group comprising: (hetero)cycloalkyl comprising from 3 to 20 atoms, (hetero)cycloalkenyl comprising from 3 to 20 atoms, and (hetero)aryl comprising from 5 to 20 atoms, said (hetero)cycloalkyl, (hetero)cycloalkenyl and (hetero)aryl preferably not substituted;
- a (hetero)cycloalkyl comprising from 3 to 20 atoms, such as a cycloheptan radical, said (hetero)cycloalkyl possibly substituted with at least one radical chosen from among (C₁-C₄) alkyls, linear or branched, such as methyl;
- a (hetero)cycloalkenyl comprising from 3 to 20 atoms, such as a cyclohexenyl radical, said (hetero)cycloalkenyl possibly substituted with at least one (C₁-C₄) alkyl radical, linear or branched, such as methyl.

According to an embodiment, in the compounds having formula (III) or (III-2), —C(R″₂)(R″₃)(R″₄), preferably represents a radical chosen from among the following radicals:

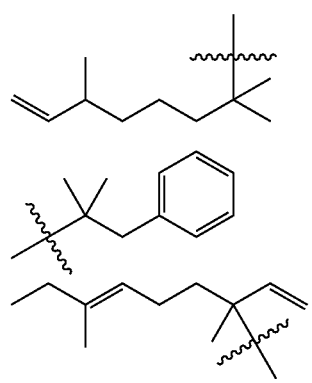

(p)

(q)

(d)

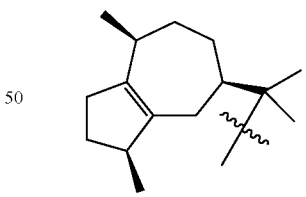

(v)

(ab)

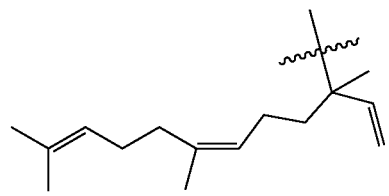

-continued (af)

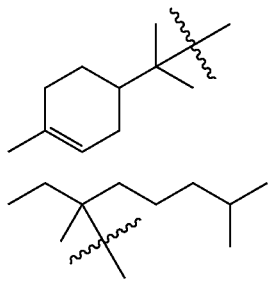

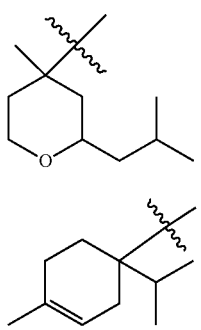

According to another embodiment, in the compounds having formula (III) or (III-2), R″$_2$ represents a (C$_1$-C$_4$) alkyl radical such as a methyl or isopropyl radical, and R″$_3$ and R″$_4$ form together with the carbon atom that carries them a cycle chosen from (hetero)cycloalkyl or (hetero)cycloalkenyl comprising from 3 to 20 atoms, said cycle possibly substituted with at least one radical chosen from among: (C$_1$-C$_4$) alkyls, linear or branched, (C$_1$-C$_4$) alkenyls, linear or branched, (C$_1$-C$_4$) alkoxy, linear or branched, and (hetero)cycloalkyls comprising from 3 to 20 atoms possibly substituted with at least one (C$_1$-C$_4$) alkyl radical.

According to an embodiment, in the compounds having formula (III) or (III-2), —C(R″$_2$)(R″$_3$)(R″$_4$), represents in particular a radical chosen from the group constituted of the following radicals:

(t)

(ae)

According to an embodiment, the compounds having formula (III) are chosen from among the following compounds having formula (III-3), as well as their salts, optical isomers, geometric isomers, and/or solvates:

(III-3)

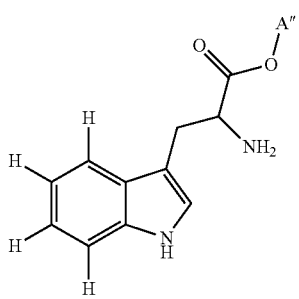

wherein A″ is such as defined hereinabove. In particular, A″ does not represent one of the following radicals:

(ah)

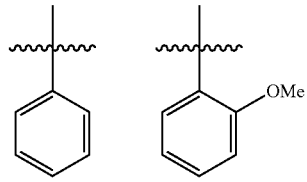

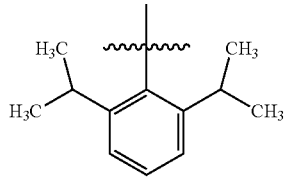
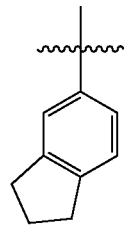 [SMILES: *c1ccc2c(c1)CCC2]

According to an embodiment, in the compounds having formula (III) or (III-3), A″ represents a (hetero)aryl radical comprising from 5 to 20 atoms, preferably an aryl radical such as phenyl, said (hetero)aryl radical possibly substituted with at least one radical chosen from among: (C$_1$-C$_4$) alkyls, linear or branched, (C$_1$-C$_4$) alkenyls, linear or branched, preferably by a (C$_1$-C$_4$) alkenyl, linear or branched, such as propenyl. In particular, A″ does not represent one of the following radicals:

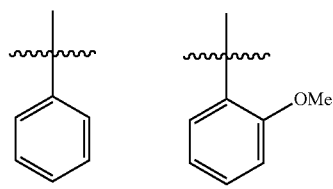

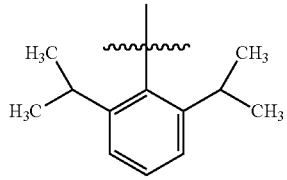

According to an embodiment, in the compounds having formula (III) or (III-3), A″ represents an aryl radical comprising from 5 to 20 atoms, with the exception of phenyl and indane, with said aryl radical possibly substituted with at least one radical chosen from among: (C$_1$-C$_4$) alkyls, linear or branched, (C$_1$-C$_4$) alkenyls, linear or branched, preferably by a (C$_1$-C$_4$) alkenyl, linear or branched, such as propenyl.

According to a preferred embodiment, in the compounds having formula (III) or (III-3), A″ preferably represents the following radical:

(r)

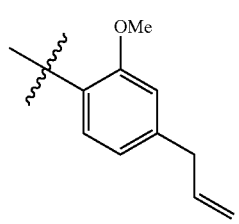

According to another embodiment, in the compounds having formula (III) or (III-3), A" represents a polycyclic radical comprising from 9 to 30 atoms, said polycyclic radical possibly substituted with at least one radical chosen from among the group comprised of $(C_1-C_6)$ alkyl radicals, linear or branched, and $(C_1-C_6)$ alkenyl radicals, linear or branched. In particular, A" does not represent:

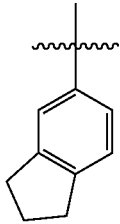

According to a preferred embodiment, A" represents one of the following radicals:

(e)

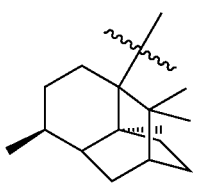

(c)

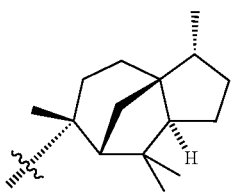

According to an embodiment, the compounds having formula (III), as well as their salts, optical and/or geometric isomers, and/or solvates, are such that R" is chosen from one of the following radicals:

(j)

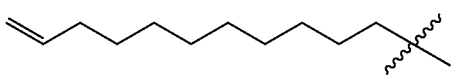

(b)

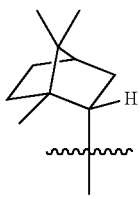

(m)

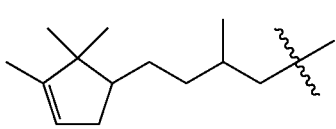

(c)

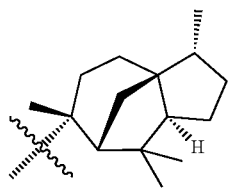

(n)

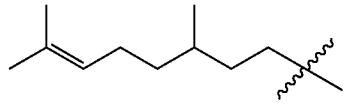

(o)

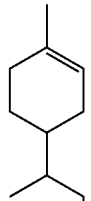

(p)

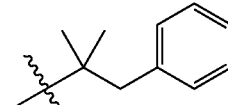

(q)

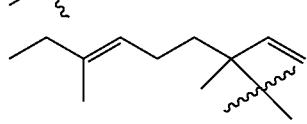

(r)

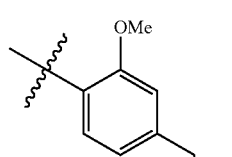

(s)

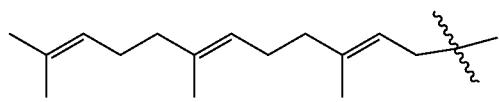

(t)

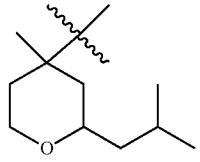

(u)

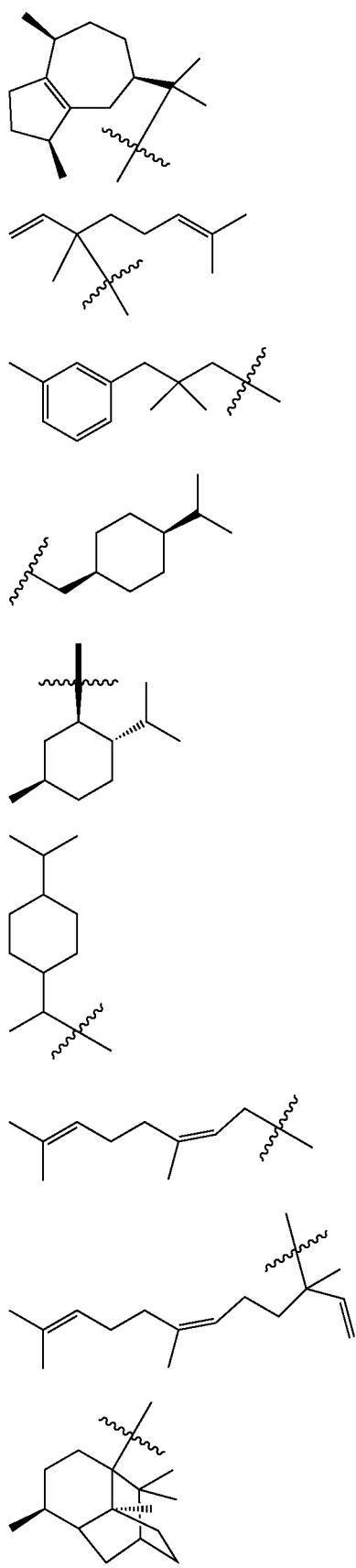
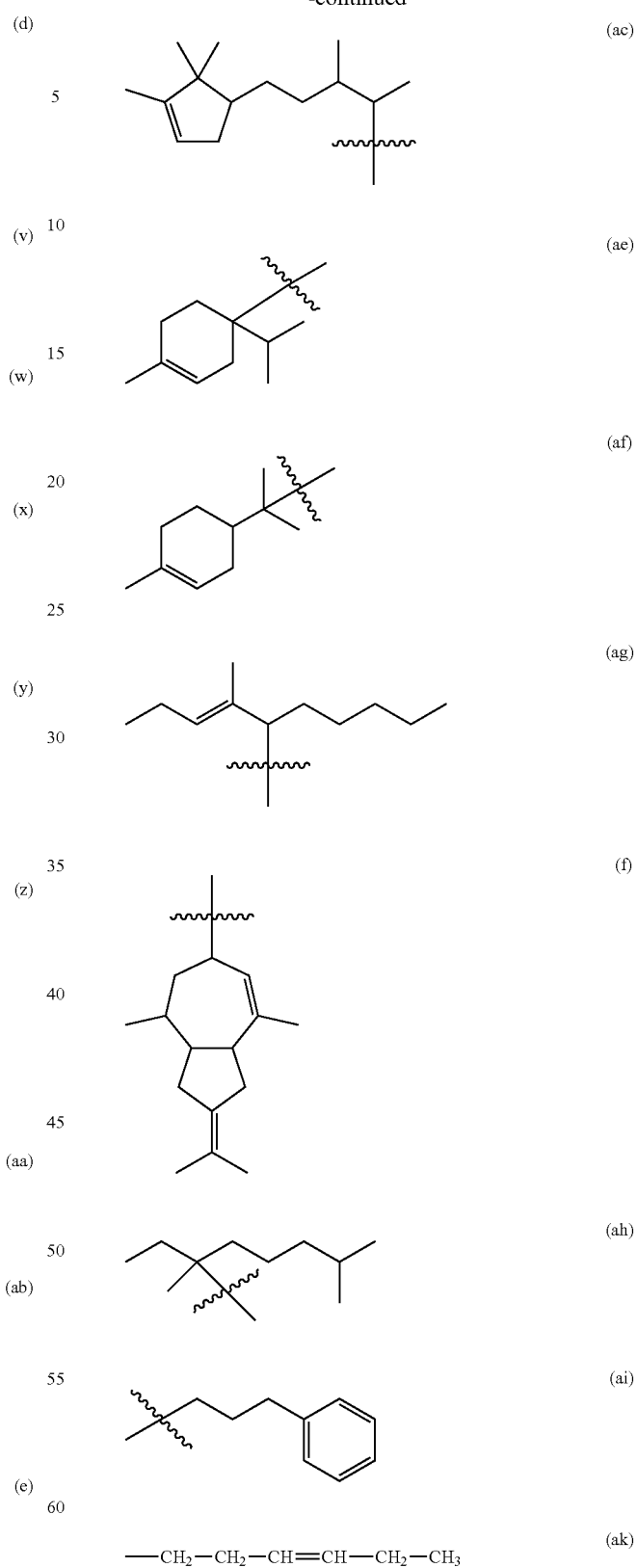
According to an embodiment, the present invention concerns the compound of formula (AD), as well as their salts, isomers and/or solvates:

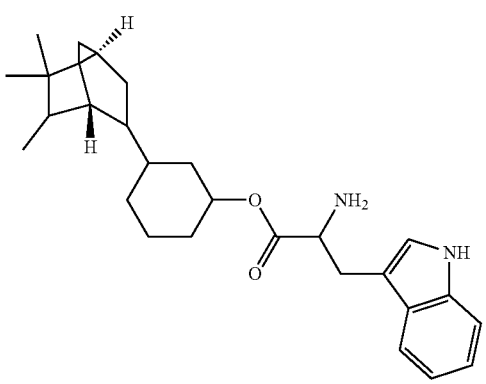 [SMILES: CC1[C@H]2C(C3CCCC(OC(=O)C(N)Cc4c[nH]c5ccccc45)C3)C[C@@H]3CC32C1(C)C]

In particular, among the preferred compounds having formula (III), mention can be made for example of the following preferred compounds:

Tryptophan cis-3-hexenyl ester of the following structure:

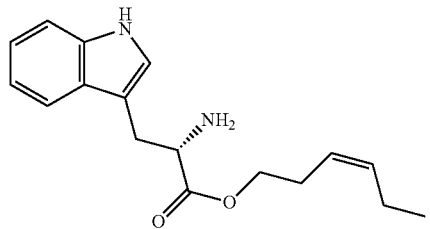

(3)

Tryptophan cis-3-hexenyl ester hydrochloride of the following structure:

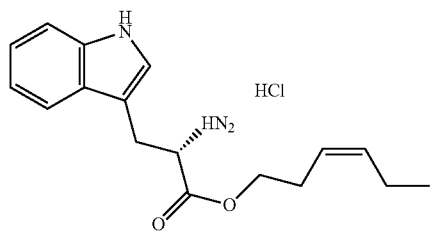

(4)

Tryptophan dihydromyrcenyl ester of the following structure:

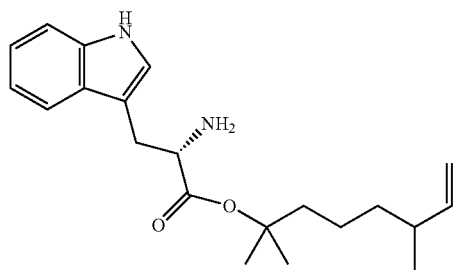

(5)

as well as their salts and/or solvates.

The expression "salts" refers to organic and inorganic acid addition salts, of the compounds of this invention. Among examples of acid addition salts, there are the addition salts of these compounds with an acid such as chlorhydrides, bromhydrides, sulfates, citrates, succinates, tartrates, lactates, tosylates, benzenesulfonates, dodecylbenzenesulfonates, phosphates and acetates preferably chlorhydrides, citrates, succinates, tartrates, phosphates, lactates.

Acid addition salts comprise amino acid salts such as glutamic acid and aspartic acid.

In particular, salts of the compounds having formula (III), are chlorhydrides.

According to this invention, "alkyl" radicals represent saturated hydrocarbon radicals, straight or branched chain, comprising unless specified otherwise, from 1 to 20, preferably from 1 to 10 carbon atoms, and preferentially from 1 to 6 carbon atoms. Mention can in particular be made, when they are linear, of the methyl, ethyl, propyl, butyl, pentyl, hexyl, octyl, nonyl and decyl radicals. Mention may particularly be made, when they are branched or substituted with one or a plurality of alkyl radicals, of isopropyl, tert-butyl, 2-ethylhexyl, 2-methylbutyl, 2-methylpentyl, 1-methylpentyl and 3-methylheptyl radicals.

According to this invention, "aryl" radicals represent aromatic mono- or bi-cycle hydrocarbons comprising, unless specified otherwise, from 5 to 20 carbon atoms. Mention can for example be made of the phenyl or naphtyl radical.

According to this invention, the term "(hetero)aryl" denotes a heteroaryl radical or an aryl radical.

According to this invention, the term "heteroaryl" denotes an aryl radical comprising one or a plurality of heteroatoms chosen from nitrogen, mono- or bi-cycle oxygen, comprising, unless specified otherwise, from 5 to 20 carbon atoms. Among the heteroaryl radicals, mention can be made of 1,3,4-oxadiazolyl.

According to this invention, the "cycloalkyl" radical is a saturated mono- or bi-cycle hydrocarbon radical, comprising, unless specified otherwise, from 3 to 20 carbon atoms, and preferably from 3 to 12 carbon atoms, such as in particular cyclopropyl, cyclopentyl or cyclohexyl.

According to this invention, the "cycloalkenyl" radical is a non-aromatic unsaturated mono- or bi-cycle hydrocarbon radical, comprising, unless specified otherwise, from 3 to 20 carbon atoms, and preferably from 3 to 12 carbon atoms, such as in particular cyclopentenyl or cyclohexenyl. When it is a bi-cycle, at least one of the cycles is non-aromatic unsaturated. In this latter case, this can for example be one of the following cycles:

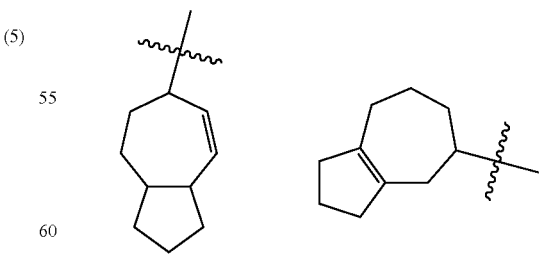

According to the invention, "bi-cycle hydrocarbon radical" denotes a hydrocarbon radical comprising two condensed hydrocarbon cycles or one bridged hydrocarbon cycle. For example, as a bi-cycle hydrocarbon radical, mention can be made of the following radicals:

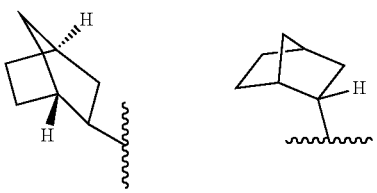 [SMILES: *C1C[C@@H]2CC23CC[C@@H]13 ; *C1CC2CCC1C2]

According to this invention, the term "(hetero)cycloalkyl" denotes a heterocycloalkyl radical or a cycloalkyl radical.

According to this invention, "heterocycloalkyl", (respectively "heterocycloalkenyl") radicals, denote the saturated, mono- or by-cycle systems (respectively unsaturated, non-aromatic), comprising, unless specified otherwise, from 3 to 20 carbon atoms, preferably from 3 to 8, containing one or several non-adjacent heteroatoms, preferably from 1 to 2 non-adjacent heteroatoms, chosen from N, O. As heterocycloalkyl, mention can in particular be made of morpholine, dioxolane, tetrahydropyran or piperazine.

According to this invention, "alkenyl" radicals represent hydrocarbon radicals, straight or branched chain, comprising one or more ethylene unsaturations. Among the alkenyl radicals, mention can be made in particular of the allyl or vinyl radicals. Preferably, and unless specified otherwise, alkenyl radicals comprise from 1 to 20 carbon atoms, preferably from 1 to 10 carbon atoms, and more preferentially from 1 to 4 carbon atoms.

According to this invention, the "alkoxy" radicals are radicals with formula —O-alkyl, the alkyl group being such as defined hereinabove. Preferably, and unless specified otherwise, the alkoxy radicals are ($C_1$-$C_4$) radicals.

According to this invention, the term "polycyclic radical" denotes a radical comprising a minimum of two hydrocarbon cycles, said radical being saturated or unsaturated non-aromatic. When the polycyclic radical is unsaturated, this means that at least one of the cycles of said polycyclic radical comprises at least one unsaturation. A polycyclic radical comprises according to an alternative from 9 to 30 atoms.

According to this invention, the term "($C_x$-$C_y$) radical" means that the radical comprises from x to y carbon atoms. For example, ($C_1$-$C_6$) alkyl radical represents an alkyl group comprising from 1 to 6 carbon atoms, or a ($C_6$-$C_{10}$) aryl radical represents an aryl group comprising from 6 to 10 carbon atoms.

According to this invention, "at least one substituent" means one or several substituents. For example, one, two, three or four substituents.

Methods for Preparing

The processes of preparation of the compounds of formulae (I), (II) or (III) disclosed in the present invention apply to the L-tryptophan as well as to the D-tryptophan or their mixtures whatever their proportions.

Compounds having formula (I) for which R designates a —$CH_2$—$R_4$ group can be obtained according to a method in 3 steps using tryptophan, in particular L-tryptophan of which the amine function is protected according to the following reaction scheme:

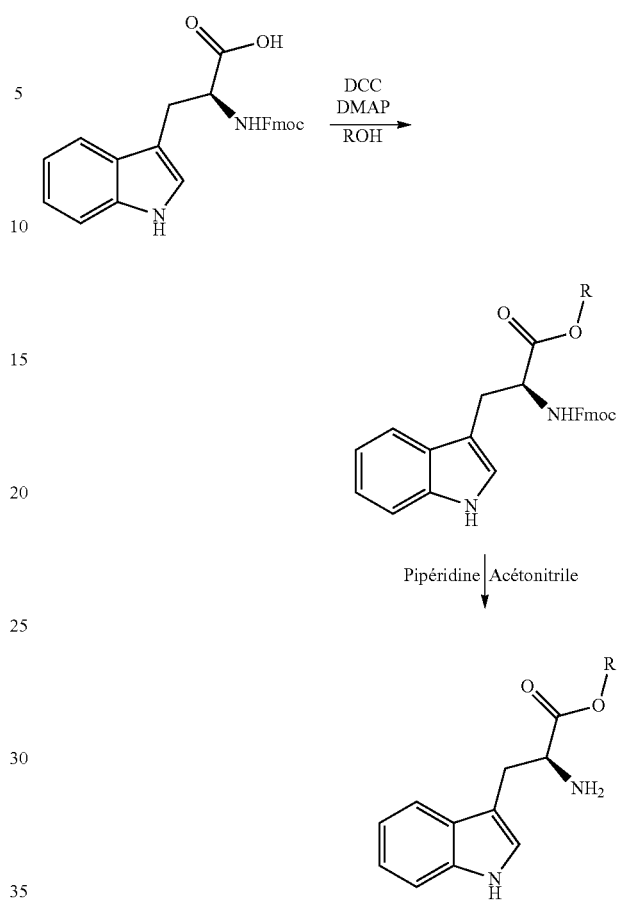

The esterification can be carried out using commercial Fmoc-tryptophan, in the presence of dimethylaminopyridine (DMAP) and of N,N'-Dicyclohexylcarbodiimide (DCC) with corresponding alcohol (ROH) in the dichloromethane. The deprotecting of the Fmoc function to result in the corresponding ester can be carried out in the acetonitrile in the presence of piperidine.

According to an embodiment, this method allows to reach compounds of formula (III-1) such as defined previously by using an alcohol R"OH.

The compounds having formula (I) for which R denotes a —C($R_2$)($R_3$)($R_4$) group where $R_2$ and $R_3$ do not simultaneously denote hydrogen, can be obtained according to a method in a single step using tryptophan, in particular L-tryptophan, according to the method of Rosowsky et al. in J. Med. Chem. 1981, 24, 1450 such as shown in the following reaction scheme:

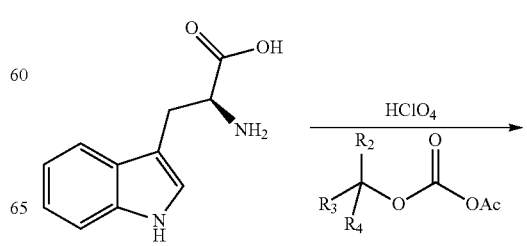

-continued

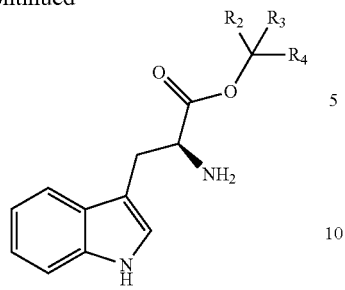

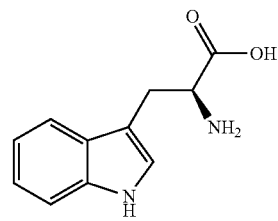

(VII)

According to an embodiment, this same method allows to reach compounds of formula (III) wherein R" designates a group —C(R"$_2$)(R"$_3$)(R"$_4$) such as previously defined.

The compounds having formula (I) for which R denotes an aromatic group can be obtained according to the method of Castro et al. Synthesis 1977, 413 using tryptophan protected by a CBz (benzyl) function, by reacting with the corresponding alcohol (ROH) in the presence of benzotri-azole-1-yl-oxy-tris-(dimethylamino)-phosphonium hexafluorophosphate then deprotecting of the CBz function by hydrogenation in the presence of palladium on carbon.

with a following compound having formula (VIII):

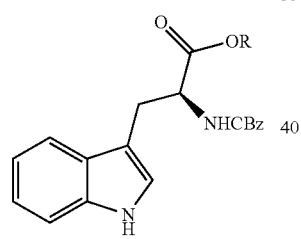

(VIII)

wherein R"$_2$, R"$_3$ and R"$_4$ are such as defined hereinabove, in the presence in particular of HClO$_4$, to result in a compound having formula (III-2).

This invention also relates to a method for preparing the aforementioned compounds having formula (III) wherein R" represents a group A" such as previously defined or having formula (III-3), said method comprising the steps of:

a) a step of reacting a compound having formula (IV)

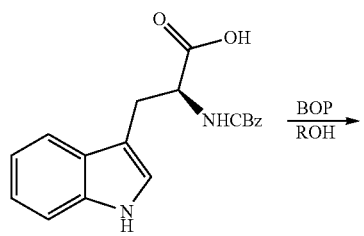

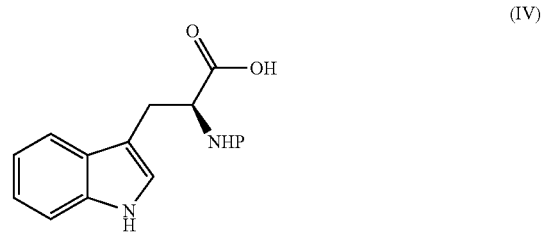

(IV)

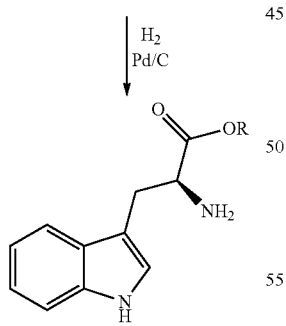

with the following compound having formula (IX) ou (IX'):

A-OH      (IX)

A"-OH      (IX")

wherein A, respectively A", is such as defined hereinabove, to result in the following compound having formula (X), respectively (X"):

According to an embodiment, this same method allows to reach compounds of formula (III) wherein R" designates a group —C(R"$_2$)(R"$_3$)(R"$_4$) such as previously defined.

This invention also relates to a method for preparing the aforementioned compounds having formula (III) wherein R" represents a group —C(R"$_2$)(R"$_3$)(R"$_4$) such as previously defined or having formula (III-2), said method comprising a step of reacting of a following compound having formula (VII):

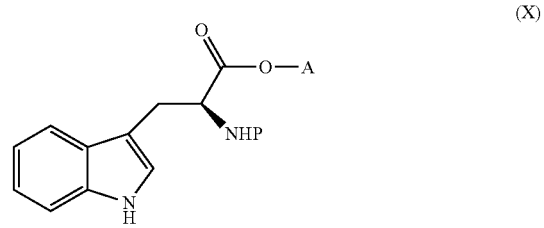

(X)

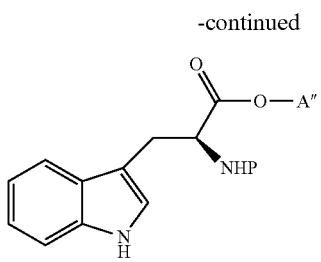

(X″)

and b) a step of deprotecting the protecting P group of a compound having formula (X), respectively (X″) in particular via catalytic hydrogenation in the presence of hydrogen and of palladium on carbon, to result in the compound having formula (III-3) such as defined hereinabove.

According to an embodiment, in the aforementioned compounds having formula (IV), P represents a protecting group chosen from among: Cbz (benzyl), BOC (tertiobutyoxycarbonyl) . . . .

Compositions

"Composition C1" denotes a composition, in particular a cosmetic composition, containing at least one compound having formula (I) possibly associated with an antiperspirant and/or one or more additional deodorant compounds.

"Composition C2" denotes a composition, in particular a cosmetic composition, containing at least one compound having formula (II) possibly associated with an antiperspirant and/or one or more additional deodorant compounds and/or one or more additional perfumes.

"Composition C3" denotes a composition, in particular a cosmetic composition, containing at least one compound having formula (III) and/or of formula (AD) possibly associated with an antiperspirant and/or one or more additional deodorant compounds and/or one or more additional perfumes.

This invention also relates to a composition, called composition 01, comprising at least one compound having formula (I) according to the invention, and one or more additional antiperspirants and/or deodorant agents other than those of formula (I), and more particularly other than those of formula (II) or (III) or formula (AD).

Preferably, composition C1 is a cosmetic composition in a physiologically acceptable medium.

According to an embodiment, composition C1 further comprises at least one cosmetic additive in particular chosen from among surfactants, preservatives, colorants, gelling agents, and thickeners.

Preferably, composition C1 is intended for topical use.

Preferably, composition C1 comprises at least one compound having formula 1 according to the invention, and one or more additional antiperspirants and/or deodorant agents other than those of formula (I), and more particularly other than those of formula (II) or (III) or formula (AD).

This invention also relates to a composition, called composition C2, comprising at least one compound having formula (II) according to the invention, and one or more additional antiperspirants and/or deodorant agents other than those of formula (I), and more particularly other than those of formula (II) or (III) or formula (AD), with said composition in particular a cosmetic composition in a physiologically acceptable medium.

Preferably, composition C2 is a cosmetic composition in a physiologically acceptable medium.

Preferably, composition C2 is intended for topical use.

According to an embodiment, composition C2 further comprises at least one cosmetic additive in particular chosen from among surfactants, preservatives, colorants, gelling agents, and thickeners.

Preferably, this invention also relates to a composition, called composition C2, comprising at least one compound having formula (II) according to the invention, and one or more additional antiperspirants and/or deodorant agents other than those of formula (I), and more particularly other than those of formula (II) or (III) or formula (AD), with said composition in particular a cosmetic composition in a physiologically acceptable medium.

This invention also relates to a composition, called composition C3, comprising at least one compound having formula (III) and/or formula (AD) according to the invention, and possibly one or more additional antiperspirants and/or deodorant agents other than those of formula (I), and more particularly other than those of formula (II) or (III) or formula (AD), with said composition in particular a cosmetic composition in a physiologically acceptable medium.

Preferably, composition C3 is intended for topical use.

According to an embodiment, composition C3 further comprises at least one cosmetic additive in particular chosen from among surfactants, preservatives, colorants, gelling agents, and thickeners.

According to an embodiment, composition C3, comprises at least one compound having formula (III) and/or formula (AD) according to the invention, and one or more additional antiperspirants and/or deodorant agents other than those of formula (I), and more particularly other than those of formula (II) or (III) or formula (AD), with said composition in particular a cosmetic composition in a physiologically acceptable medium.

Compositions C1, C2 or C3 according to the invention can comprise compounds respectively having formula (I), (II) and/or (III) and/or formula (AD) in mass concentrations ranging from 0.01% to 10%, preferably from 0.05% to 5%, and preferentially from 0.1% to 5%, as total weight of these compounds in relation to the total weight of said compositions.

In the framework of the invention, and unless specified otherwise, the term "physiologically acceptable medium" denotes a medium suitable for administering a composition by the topical route. A physiologically acceptable medium is preferentially a cosmetically acceptable medium, i.e. free from odor, or unpleasant appearance, and which is perfectly compatible with the topical administration route. In the present case where the composition is intended to be administered by the topical route, i.e. by applying on the surface of the keratin material in question, such a medium is particularly considered to be physiologically acceptable when it does not give rise to discomfort during the application or after the application, that is unacceptable for the user.

The physiologically acceptable medium is generally suitable for the nature of the support to which the composition should be applied, and also for the way in which the composition is to be packaged.

Additional Deodorant Agents

Additional deodorant agents, other than the compounds of the invention, can be bacteriostatic agents or bactericidal agents acting on germs of underarm odor, such as 2,4,4'- trichloro-2'-hydroxydiphenylether (Triclosan), 2,4-dichloro-2'-hydroxydiphenylether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (Farnesol); quaternary ammonium salts such as cetyltrimethylammonium salts, cetylpyridinium salts; polyols such as those of the glycerin type, 1,3-propanediol (ZEMEA PROPANEDIOL® sold by Dupont Tate and Lyle Bioproducts), 1,2-decanediol (SYMCLARIOL® from Symrise); glycerin derivatives such as for example Caprylic/Capric Glycerides (CAPMUL MCM® from Abitec), Caprylate or glyceryl caprylate (DERMOSOFT GMCY® and DERMOSOFT GMC® respectively from STRAETMANS), Polyglyceryl-2 Caprate (DERMOSOFT DGMC® from STRAETMANS) biguanide derivatives such as polyhexamethylene biguanide salts; chlorhexidine and salts; 4-Phenyl-4,4-dimethyl-2butanol (SYMDEO MPP® from Symrise); cyclodextrins; chelating agents such as Tetrasodium Glutamate Diacetate (CAS #51981-21-6) sold under the trade name DISSOLVINE GL-47-S® from Akzo Nobel, EDTA (Ethylendiamino Tetraacetic acid) and DPTA (1,3-diaminopropanetetraacetic acid).

Among the deodorant agents according to the invention, the following can also be mentioned:

zinc salts such as zinc salicylate, zinc phenolsulfonate, zinc pyrrolidone carboxylate (more commonly referred to as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc acetate or mixtures thereof;

odor absorbers such as zeolites, in particular metalks without silver, cyclodextrins, metal oxide silicates such as those described in the application US2005/063928; metal oxide particles modified by a transition metal such as those described in the applications US2005084464 and US2005084474, aluminosilicates such as those described in the application EP1658863, chitosan derivative particles such as those described in the patent U.S. Pat. No. 6,916,465;

sodium bicarbonate;

salicylic acid and its derivatives such as n-octanoyl-5-salicylic acid;

alun;

triethyl citrate

The additional deodorant agents can be present preferably in the compositions $C_1$, C2 or C3 according to the invention in mass concentrations ranging from 0.01% to 10%, preferably from 0.05% to 5%, and preferentially from 0.1% to 5%, by weight in relation to the total weight of the composition.

Antiperspirant Agents

Among the antiperspirant agents, mention can be made of aluminum and/or zirconium antiperspirant salts or complexes, preferably chosen from aluminum and zirconium halohydrates, zirconium hydroxychloride and aluminum hydroxychloride complexes with or without an amino acid such as those described in U.S. Pat. No. 3,792,068.

Among the aluminum salts mention can be made of aluminum chlorhydrate in activated or non-activated form, aluminum chlorhydrex, aluminum chlorhydrex polyethyleneglycol complex, aluminum chlorhydrex propyleneglycol, aluminum dichlorhydrate, aluminum dichlorohydrex polyethyleneglycol, aluminum dichlorohydrex polypropyleneglycol, aluminum sesquichlorhydrate, aluminum sesquichlorohydrex polyethylene glycol, aluminum sesquichlorohydrex propyleneglycol, aluminum salts buffered by aluminum and sodium lactate.

Among the aluminum and zirconium salts mention can be made in particular of aluminum zirconium octachlorohydrate, aluminum zirconium pentachlorohydrate, aluminum zirconium tetrachlorohydrate, aluminum zirconium trichlorohydrate.

Zirconium hydroxychloride and aluminum hydroxychloride complexes with an amino acid are generally known under the name ZAG (when the amino acid is glycine). Among these products, mention can be made of the complexes of aluminum zirconium octachlorohydrex glycine, aluminum zirconium pentachlorohydrex glycine, aluminum zirconium tetrachlorohydrex glycine and aluminum zirconium trichlorohydrex glycine. Aluminum sesquichlorohydrate is in particular sold under the trade name REACH 301® by SUMMITREHEIS.

Among the complexes of aluminum and zirconium, mention can be made of the complexes of zirconium hydroxychloride and aluminum hydroxychloride with an amino acid such as glycine having for name INCI: Aluminum zirconium tetrachlorohydrex Gly for example that sold under the trade name REACH AZP-908-SUF® by Summitreheis.

Use will be made more particularly of aluminum chlorhydrate sold under the trade names LOCRON S FLA®, LOCRON P, LOCRON L.ZA by CLARIANT; under the trade names MICRODRY ALUMINIUM CHLOROHYDRATE®, MICRO-DRY 323®, CHLORHYDROL 50, REACH 103, REACH 501 by Summitreheis; under the trade name WESTCHLOR 200® by Westwood; under the trade name ALOXICOLL PF 40® by GUILINI CHEMIE; CLURON 50%® by Industria Quimica Del Centro; CHLOROHIDROXIDO ALUMINIO SO A 50%® by FINQUIMICA.

AS another antiperspirant agent, mention can be made of the expanded perlite particles such as those obtained by the method of expansion described in patent U.S. Pat. No. 5,002,698. The perlites that can be used according to the invention are generally aluminosilicates of volcanic origin and have as composition:

70.0-75.0% by weight of silica $SiO_2$;
12.0-15.0% by weight of aluminum oxide $Al_2O_3$;
3.0-5.0% of sodium oxide $Na_2O$;
3.0-5.0% of potassium oxide $K_2O$;
0.5-2% of iron oxide $Fe_2O_3$;
0.2-0.7% of magnesium oxide MgO;
0.5-1.5% of calcium oxide CaO;
0.05-0.15% of titanium oxide $TiO_2$.

Preferably, the particles of perlite used will be ground; they are in this case referred to as Expanded Milled Perlite (EMP). They preferably have a particle size defined by a median diameter D50 ranging from 0.5 to 50 μm, and preferably from 0.5 to 40 μm.

Preferably, the particles of perlite used have a loose bulk apparent density at 25° C. ranging from 10 to 400 kg/m3 (Standard DIN 53468), and preferable from 10 to 300 kg/m3.

Preferably, the particles of expanded perlite according to the invention have a water absorption capacity measured at the WET POINT ranging from 200 to 1500%, and preferably from 250 to 800%.

The wet point corresponds to the quantity of water that must be added to 1 g of particle in order to obtain a homogeneous paste. This method is derived directly from that of oil take-up applied to solvents. The measurements are taken in the same way by the intermediary of the Wet Point and of the Flow Point having respected the following definition:

WET POINT: mass expressed in grams for 100 g of product corresponding to the obtaining of a homogeneous paste during the addition of a solvent to a powder.

FLOW POINT: mass expressed in grams for 100 g of product starting from which the quantity of solvent is greater than the capacity of the powder to retain it. This results in the obtaining of a more or less homogeneous mixture flowing on the sheet of glass.

The Wet Point and the Flow Point can be measured according to the following protocol:

Protocol for measuring the absorption of water:
1) Equipment Used
Sheet of glass (25×25 mm)
Spatula (wooden handle and metal portion (15×2.7 mm)
Silk bristle brush
Scale
2) Procedure The sheet of glass is placed on the scale and 1 g of particles of perlite is weighed. The beaker containing the solvent as well as the sampling liquipipette are placed on the scale. The solvent is added progressively to the powder by mixing the whole regularly (every 3 to 4 drops) using the spatula.

Note the mass of the solvent required to obtain the Wet Point. The solvent is added again and note the mass making it possible to reach the Flow Point. Take the average over 3 tests.

Use will be made in particular of the particles of expanded perlite sold under the trade names OPTIMAT 1430 OR or OPTIMAT 2550 by WORLD MINERALS.

The antiperspirant agents may be present in the compositions C1, C2 or C3 according to the invention at a rate of 0.001 to 30% by weight in relation to the total weight of the composition, and preferably at a rate of 0.5 to 25% by weight.

Dosage Forms

The compositions C1, C2 or C3 according to the invention may be presented in any of the dosage forms conventionally used for topical application and particularly in the form of aqueous gels, aqueous or hydroalcoholic solutions. They may also, by adding a fatty or oil phase, be presented in the form of dispersions such as lotion, emulsions of liquid or semi-liquid consistency such as milk, obtained by dispersing a fatty phase in an aqueous phase (O/W) or conversely (W/O), or suspensions or emulsions of soft, semi-solid or solid consistency such as cream or gel, or multiple emulsions (W/O/W or O/W/O), microemulsions, ionic and/or non-ionic type vesicle dispersions, or wax/aqueous phase dispersions. These compositions are prepared according to routine methods.

The compositions C1, C2 or C3 may be particularly packaged in pressurized form in an aerosol device or in a pump bottle; packaged in a device equipped with a perforated wall particularly a grid; packaged in a device equipped with a roll-on applicator; packaged in stick form, in loose or compact powder form. In this respect, they contain the ingredients generally used in this type of products and well-known to those skilled in the art.

According to a further specific form of the invention, the compositions C1, C2 or C3 according to the invention may be anhydrous.

Preferably, the compositions C1, C2 or C3 according to the invention are anhydrous.

In the framework of the invention, the term "anhydrous composition" denotes a composition containing less than 2% by mass of water, or less than 0.5% of water, and particularly free from water, water not being added during the preparation of the composition but corresponding to the residual water provided by the mixed ingredients.

According to a further specific form of the invention, the compositions according to the invention may be solid particularly in stick form.

In the framework of the invention, the term "solid composition" denotes that the measurement of the maximum force measured by means of texturometric analysis on inserting a probe in the sample of formula should be at least equal to 0.25 Newton, in particular at least equal to 0.30 Newton, particularly at least equal to 0.35 Newton, assessed under precise measurement conditions as follows.

The formulas are poured when heated into jars 4 cm in diameter and 3 cm at the bottom. Cooling is performed at ambient temperature. The hardness of the formulas produced is measured after waiting 24 hours. The jars containing the samples are characterized by means of texturometric analysis using a texturometer such as that marketed by Rheo TA-XT2, according to the following protocol: a 5 mm diameter stainless steel ball type probe is brought into contact with the sample at a speed of 1 mm/s. The measurement system detects the interface with the sample with a detection threshold equal to 0.005 Newtons. The probe is inserted 0.3 mm into the sample, at a rate of 0.1 mm/s. The measurement apparatus records the progression of the compression force measured over time, during the penetration phase. The hardness of the sample corresponds to the mean of the maximum values of the force detected during penetration, for at least 3 measurements.

Aqueous Phase

Compositions C1, C2 or C3 according to the invention may comprise at least one aqueous phase. They are particularly formulated in aqueous lotions or in water-in-oil, oil-in-water emulsion, or in multiple emulsion (triple oil-in-water-in-oil or water-in-oil-in-water) (such emulsions are known and described for example by C. FOX in "Cosmetics and Toiletries"—November 1986—Vol 101—pages 101-112).

The aqueous phase of said compositions C1, C2 or C3 may contain water and generally further water-soluble or miscible solvents. The water-soluble or miscible solvents may comprise short-chain mono-alcohols for example $C_1$-$C_4$ such as ethanol, isopropanol; diols or polyols such as ethyleneglycol, 1,2-propyleneglycol, 1,3-butylene glycol, hexyleneglycol, diethyleneglycol, dipropylene glycol, 2-ethoxyethanol, diethylene glycol monomethylether, triethylene glycol monomethylether and sorbitol. Propyleneglycol and glycerin, propane 1,3 diol shall more particularly be used.

When the composition is in the form of emulsion, it generally contains according to the nature of the emulsion one or a plurality of emulsifying surfactants.

The total quantity of emulsifiers shall be preferably in the compositions C1, C2 or C3 according to the invention at active substance concentrations ranging from 1 to 8% by mass and more particularly from 2 to 6% by mass in relation to the total mass of the composition C1, C2 or C3.

Fatty Phase

The compositions C1, C2 or C3 according to the invention may contain at least one non-water-miscible organic liquid phase, known as a fatty phase. This generally includes one or a plurality of hydrophobic compounds rendering said phase non-miscible in water. Said phase is liquid (in the absence of a structuring agent) at ambient temperature (20-25° C.). Preferentially, the non-water-miscible organic liquid phase according to the invention generally comprises at least one volatile oil and/or a non-volatile oil and optionally at least one structuring agent.

The term "oil" denotes a liquid fat at ambient temperature (25° C.) and atmospheric pressure (760 mm Hg i.e. $1.05 \times 10^5$ Pa). The oil may be volatile or non-volatile.

The term "volatile oil" according to the invention denotes any oil capable of evaporating on contact with skin or keratin fiber, in less than one hour, at ambient temperature and at atmospheric pressure. The volatile oils according to the invention are volatile cosmetic oils, which are liquid at ambient temperature, having a vapor pressure different to zero, at ambient temperature and atmospheric pressure, particularly ranging from 0.13 Pa to 40,000 Pa ($10^{-3}$ at 300 mm Hg), particularly ranging from 1.3 Pa to 13,000 Pa (0.01 to 100 mm Hg), and more specifically ranging from 1.3 Pa to 1300 Pa (0.01 at 10 mm Hg).

The term "non-volatile oil" denotes an oil remaining on skin or keratin fiber at ambient temperature and atmospheric pressure for at least several hours and particularly having a vapor pressure less than $10^{-3}$ mm Hg (0.13 Pa).

The oil may be chosen from any physiologically acceptable and particularly cosmetically acceptable oils, in particular mineral, animal, plant, synthetic oils; in particular, volatile or non-volatile hydrocarbon and/or silicone and/or fluorinated oils and mixtures thereof.

More specifically, the term "hydrocarbon oil" denotes an oil essentially comprising carbon and hydrogen atoms and optionally one or a plurality of functions chosen from hydroxyl, ester, ether, carboxylic functions. Generally, the oil has a viscosity of 0.5 to 100,000 mPa·s, preferably from 50 to 50,000 mPa·s and more preferably from 100 to 300,000 mPa·s.

By way of examples of volatile oils suitable for use in the invention, mention may be made of:

volatile hydrocarbon oils chosen from hydrocarbon oils having 8 to 16 carbon atoms, and particularly petroleum-based $C_8$-$C_{16}$ isoalkanes (also referred to as isoparaffins) such as isododecane (also referred to as 2,2,4,4,6-pentamethylheptane), isodecane, isohexadecane, and for example the oils sold under the trade names Isopars or Permetyls, $C_8$-$C_{16}$ branched esters, iso-hexyl neopentanoate, and mixtures thereof.

volatile silicones, such as for example volatile linear or cyclic silicone oils, particularly those having a viscosity≤8 centistokes (8 $10^{-6}$ m$^2$/s), and having in particular 2 to 7 silicon atoms, these silicones optionally comprising alkyl or alkoxy groups having 1 to 10 carbon atoms, and mixtures thereof.

Mention may be made, as a volatile silicone oil suitable for use in the invention, in particular, of octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane, dodecamethyl pentasiloxane, and mixtures thereof.

plant-based hydrocarbon oils such as liquid fatty acid triglycerides having 4 to 24 carbon atoms such as heptanoic or octanoic triglycerides or wheat germ, olive oils, sweet almond, palm, rapeseed, cotton, alfalfa, poppy seed, pumpkin, squash, blackcurrant seed, evening primrose, millet, barley, quinoa, rye, safflower, candlenut, passiflora, musk rose, sunflower, corn, soybean, squash, grape seed, sesame, hazelnut, apricot, macadamia, castor, avocado oils, caprylic/capric acid triglycerides such as those sold by Stearineries Dubois or those sold under the trade names Miglyol 810, 812 and 818 by Dynamit Nobel, jojoba oil;

linear or branched hydrocarbons of mineral or synthetic origin, such as liquid paraffins and derivatives thereof, petroleum jelly, polydecenes, polybutenes, hydrogenated polyisobutene such as Parleam, squalane;

synthetic ethers having 10 to 40 carbon atoms such as dicaprylether;

synthetic esters particularly of fatty acids such as the oils having the formula $R^1COOR^2$ wherein $R^1$ represents the residue of a linear or branched higher fatty acid comprising 1 to 40 carbon atoms and $R^2$ represents a hydrocarbon chain, particularly branched containing 1 to 40 carbon atoms where $R^1+R^2 \geq 10$ such as isononyl isononanoate, isopropyl myristate, isopropyl palmitate, $C_{12}$ to $C_{15}$ alcohol benzoate, liquid fatty alcohols at ambient temperature with a branched and/or unsaturated carbon chain having 12 to 26 carbon atoms such as octyl dodecanol;

silicone oils, such as polydimethylsiloxanes (PDMS) which are non-volatile, linear (dimethicone) or cyclic (cyclomethicones); polydimethylsiloxanes comprising alkyl, alkoxy or phenyl groups which are pendant or at the end of the silicone chain, said groups having 2 to 24 carbon atoms; phenylated silicones, such as phenyl trimethicones, phenyl dimethicones, phenyltrimethylsiloxydiphenylsiloxanes, diphenyl dimethicones, diphenylmethyldiphenyl-trisiloxanes or (2-phenylethyl)trimethylsiloxysilicates, and mixtures thereof.

Cosmetic Compositions

The present invention also relates to a cosmetic composition including, in a physiologically acceptable medium, a composition C1, C2 or C3 such as defined above.

The cosmetic compositions C2 or C3 are in particular perfuming compositions. They can for example be packaged in the form of bottles, spray bottles, pump bottles, roll on, tubes. They can be also applied in the form of fine particles by means of pressurization devices. The devices suitable for the invention are typically those known to those skilled in the art and comprise non-aerosol pumps or "atomizers", aerosol containers comprising a propellant and aerosol pumps using compressed air as a propellant.

The expressions "between . . . and . . . " and "ranging from . . . to . . . " are to be understood to be inclusive of the limits, unless specified otherwise.

The following examples make it possible to illustrate the invention without however limiting it.

In the examples, the temperature is ambient (20-25° C.), the pressure atmospheric (101,325 Pa), unless specified otherwise. The mass of the ingredients is expressed as a percentage in relation to the mass of the total composition in question.

EXAMPLES

A. Preparing the Compounds

Example A-1

Preparing the Compound 1

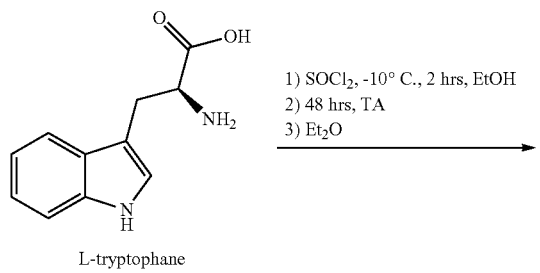

L-tryptophane

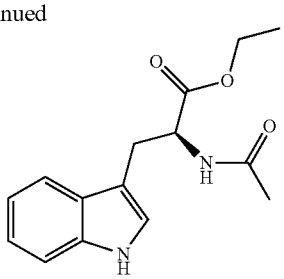

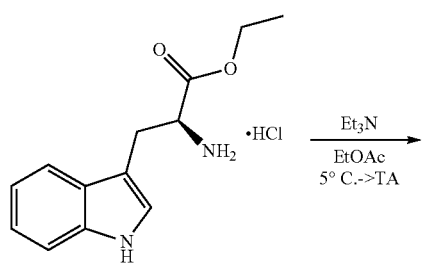

Composé 1

L-tryptophan ethyl ester chlorhydride (compound 1) was obtained as described in *Synthesis of substituted dipeptide GB-115 as a potential selective anxiolytic* Kir'yanova, E. P. et al *Pharmaceutical Chemistry Journal*, 45(2), 103-106; 2011. It can be obtained by treatment of the L-tryptophan with thionyl chloride at −10° C. in ethanol, cold stirring for 2 hours and at ambient temperature (about 25° C.) for 48 hours. After adding ether, the salt crystallizes.

Example A-2

Preparing the Compound 2 Described in WO 2006/119283

(2)

The ethyl N-Acetyl-L-tryptophanate (compound 2) can be obtained as described in patent CN 102351775 by acetylation of the compound 1. The acetylation can be carried out in ethyl acetate by treatment with triethylamine at 5° C. then stirring at ambient temperature for 1 hour.

Example A-3

Preparing the Compound 3 (Tryptophan cis-3-hexenyl ester)

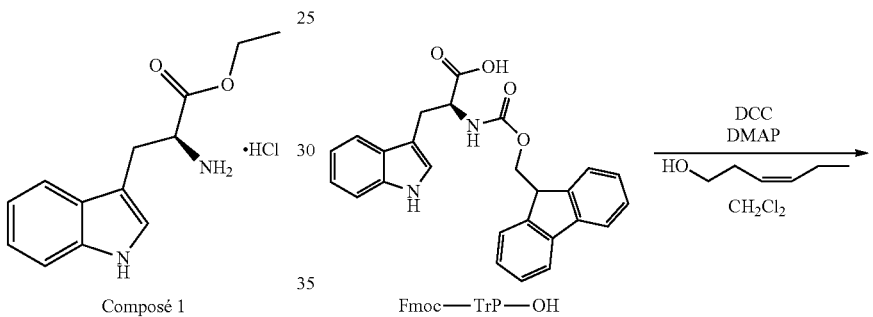

Fmoc—TrP—OH

B

To a solution of commercial Fmoc-Trp-OH (50 g) in dichloromethane (1 l) are added cis-hexenol (13.1 ml), dimethylaminopyridine (1.42 g) and N,N'-dicyclohexylcarbodiimide (24.6 g) heated beforehand using a hot water bath. The medium is stirred during the night at ambient temperature. A CCM control as well as an LCMS conducted using an aliquote show the presence of the product desired and the absence of alcohol. The mixture is filtered over celite. After rinsing with dichloromethane, the filtrate is dry concentrated to result in a gross product (68.3 g). The product is co-evaporated with methanol (150 ml) in order to eliminate the residual dichloromethane then the solution is dry concentrated (65.8 g). a purification via silica gel chromatography is carried out (deposit and eluent DCM 100%). The product obtained is solubilized in ethyl acetate. After concentration of the solution, the yellow oil obtained is crushed in pentane (2 1). The suspension is filtered and the solid is rinsed with pentane then dried in a vacuum twice to result in the product B desired: white solid—30 g—yield 50%.

Analyses: ¹H-RMN (MeOD, 300 MHz), ¹³C-RMN (MeOD, 75 MHZ), LCMS, elemental analysis and CPG confirm the obtaining of the desired compound.

Example A-4

Preparing the Compound 4 (Tryptophan cis-3-hexenyl ester) hydrochloride

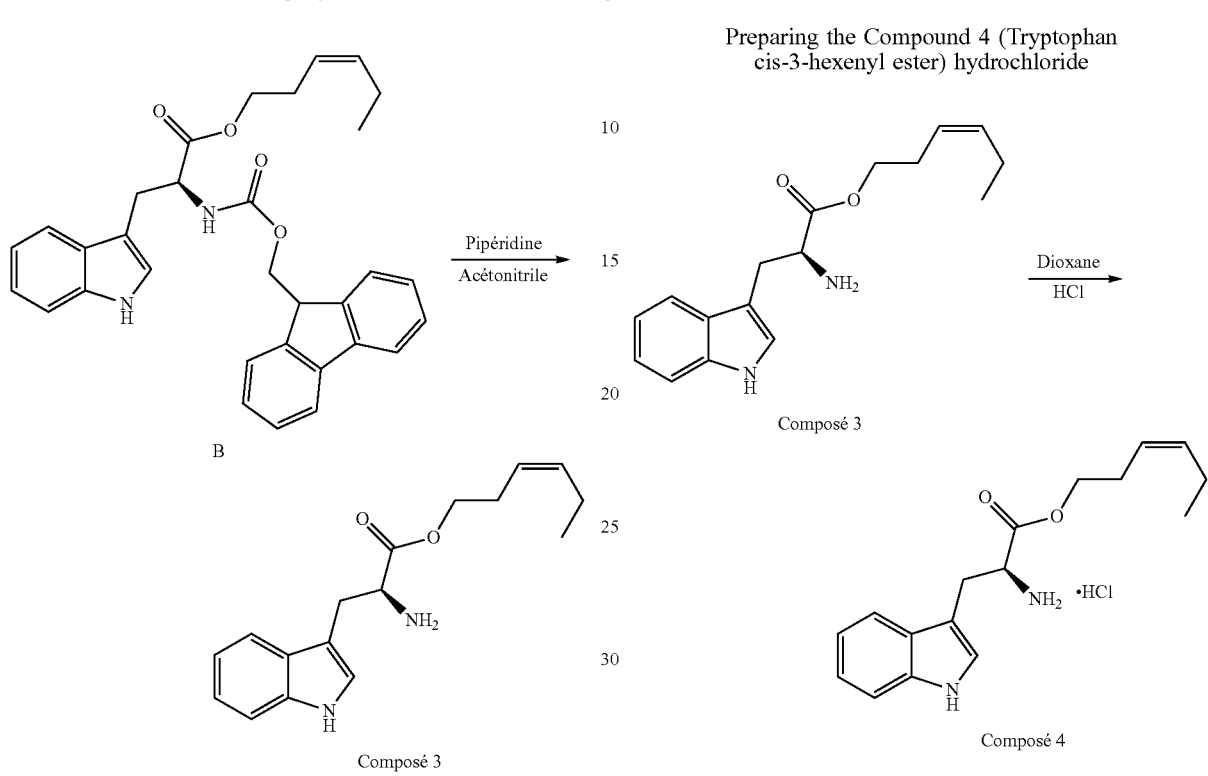

To a solution of the compound B (30 g) in acetonitrile (450 ml) piperidine (58 ml) is added in 3 minutes. After 10 minutes of stirring, the formation of a white precipitate is observed. A CCM control (heptane/AcOEt 7/3) shows that the reaction is complete. The mixture is filtered. The filtrate is dry concentrated then co-evaporated 3 times using toluene to result in a gross product: beige solid—32 g. After several purifications via silica gel chromatography (DCM deposit, DCM/MeOH gradient), the desired product containing traces of dichloromethane and hexanol is obtained (batch 356-150-C2C2, 11.56 g). Several successive co-evaporations in a vacuum (0.6-1 mbar) with dichloromethane and pentane are carried out in order to eliminate the residual hexanol. The desired compound 3 is obtained: oil that crystallizes—5.94 g—yield 35%.

To a solution of the compound 3 (5.24 g) in dioxane (15 ml) cooled by a chilled water bath is added a solution of 4M hydrochloric acid in the dioxane (4.48 ml) resulting in the formation of a precipitate. Pentane (75 ml) is added and the mixture is crushed for 10 minutes the filtered. The filtrate is concentrated in a vacuum then water is added. The suspension is subjected to ultrasound then freeze dried to result in the compound 4 desired: white solid—5.6 g—yield 95%.

Analyses: ¹H-RMN (MeOD, 300 MHz), ¹³C-RMN (MeOD, 75 MHZ), LCMS and elemental analysis confirm the obtaining of the desired compound.

Example A-5

Preparing the Compound 5 (Tryptophan dihydromyrcenyl ester)

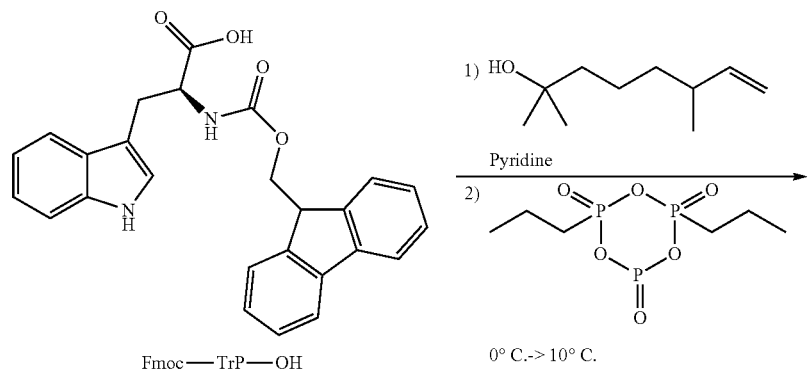

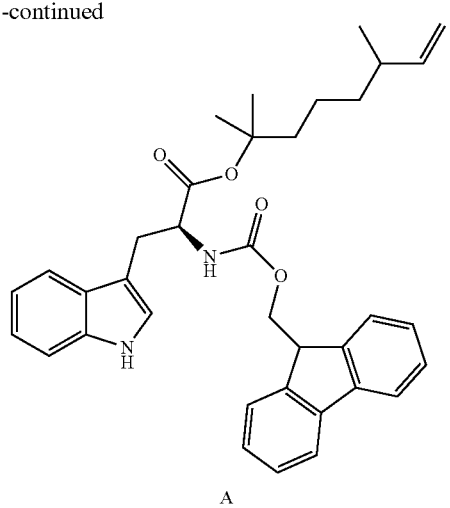

A

To a solution of commercial Fmoc-Trp-OH (38 g) in pyridine (190 ml) is added dihydromyrcenol (27.8 g). The medium is cooled by a chilled water bath before adding 1-propylphosphonic cyclic anhydride (113 g). Exothermicity is observed during the adding (Tmedium=10° C.). After return to ambient temperature, the medium is stirred during the night in nitrogen. The soluble yellow mixture becomes red. An LCMS carried out using an aliquote shows the presence of 3 products. The medium is concentrated at 38° C. to result in a gross product (149.5 g). A CCM control (heptane/AcOEt 9/1) shows the presence of the desired product, initial alcohol and pyridine. A purification via silica gel chromatography (DCM deposit, heptane/AcOEt gradient) followed by a co-evaporation with acetonitrile in order to eliminate the residual ethyl acetate resulting in the product A desired: white solid—43.5 g—yield 86%.

Analyses: $^1$H-RMN (MeOD, 300 MHz) confirms the obtaining of the expected compound.

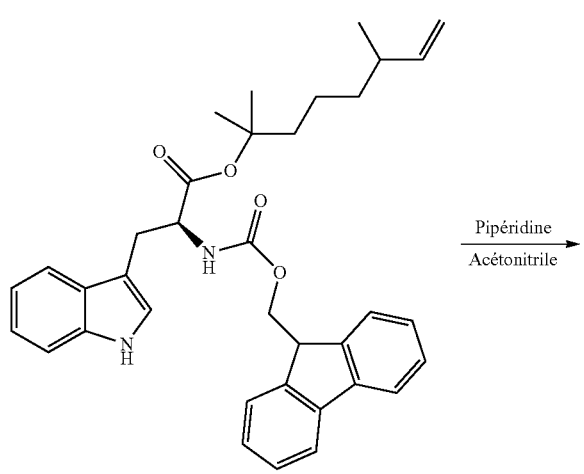

Pipéridine
Acétonitrile

-continued

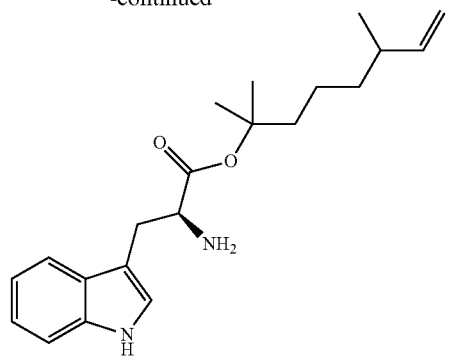

Composé 5

To a solution of the compound A (43.5 g) in acetonitrile (650 ml) piperidine (76 ml) is added. The stirring is maintained for 10 minutes. The medium, initially soluble of yellow color, precipitates out little by little. A CCM control (heptane/AcOEt 7/3) shows that the reaction is complete. The medium is filtered and the filtrate is concentrated then co-evaporated with toluene to result in a gross product (48.4 g). A purification via silica gel chromatography (DCM deposit, DCM/MeOH gradient) to result in the product 5 desired: orange oil—10.5 g—yield 76%.

Analyses: $^1$H-RMN (MeOD, 300 MHz), $^{13}$C-RMN (MeOD, 75 MHZ), LCMS and elemental analysis confirm the obtaining of the desired compound.

Example A-6

Compounds 6, 7 and 8

These compounds are commercial. Compound 6 and 8 are available at SANTA CRUZ BIOTECHNOLOGY and compounds 7 and 8 are available at Sigma Aldrich.

Compound 7 can be obtained as described in *J. Org. Chem.*, 1983, 48 (1), pp 121-123

Compound 6

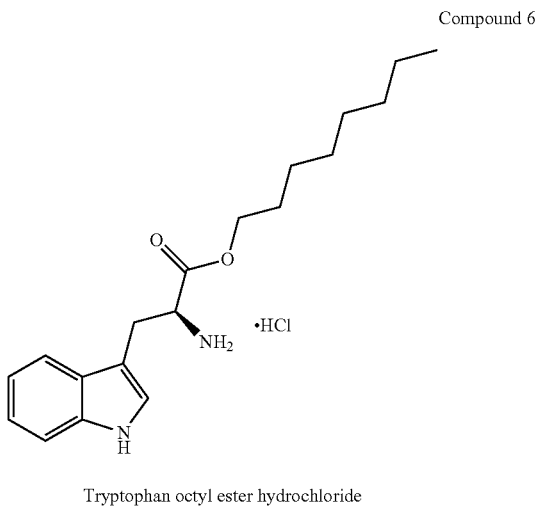

Tryptophan octyl ester hydrochloride

Compound 7

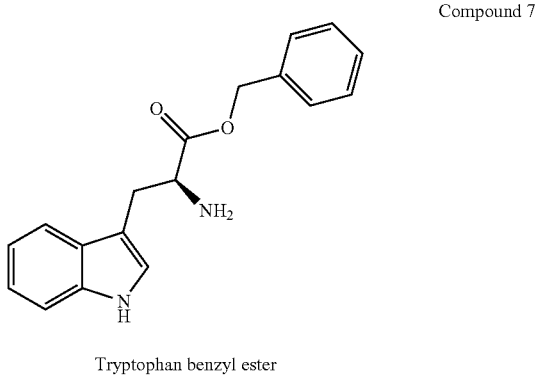

Tryptophan benzyl ester

Compound 8

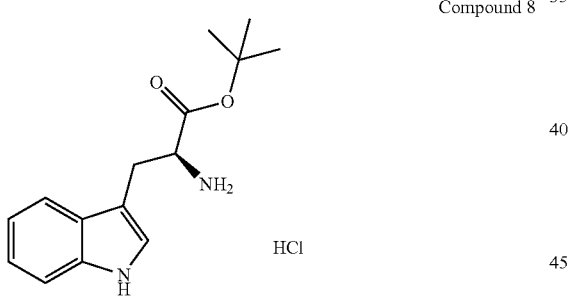

Tryptophan tertiobutyl ester hydrochloride

B. Activities of the Compounds

Example B-1

Study of the Anti-Microbial/Bactericidal Effects

The anti-microbial activity of Tryptophan ethyl ester hydrochloride (compound 1) was valuated in vitro on *Corynebacterium xerosis* (killing test, quantity of micro-organisms killed).

Purpose of test: Quantitative determination of the activity of a cosmetic starting material with respect to *Corynebacterium xerosis*, a micro-organism involved in the phenomena linked to underarm odor. This micro-organism is placed in optimum growth conditions.

Protocol: The model strain used is: *Corynebacterium xerosis* CIP 5216 (bacteria)

The strain is placed into contact with the starting material to be tested in a suitable liquid culture medium. The dilutions of the compounds under evaluation are performed in agar at 1:1000, making it possible, for dispersible compounds under evaluation, to do away with the use of a solvent which could introduce bias in the evaluation of the compounds. In parallel, a growth control, in which the starting material to be tested is replaced with diluent, is prepared in the same conditions.

The samples are placed in a rotating incubator at 35° C. and maintained under stirring for the entire duration of the test.

After 2, 6 and 24 hours of contact, the number of viable micro-organisms remaining in the mixture is evaluated.

The results are expressed as a logarithm of the number of micro-organisms per milliliter of mixture.

Results: The results (change in the number of viable micro-organisms per milliliter of sample, in log) are presented in the table hereinbelow:

| GERMS | Inoculum CFU/g of preparation | (T0M/TA) CFU/g of preparation | | |
|---|---|---|---|---|
| | | 2 hours | 6 hours | 24 hours |
| *CORYNEBACTERIUM XEROSIS* | 1.4E7 | 4.6E3 | 4.0E1 | <20 |

In terms of the growth control, Tryptophan ethyl ester hydrochloride at 0.5%, has excellent anti-microbial activity on *C. xerosis*. A reduction of 3.3 Log Units after 2 h of contact, of 5.4 Log after 6 h is noted. After 24 h of contact, the reduction is greater than or equal to 6.6 Log.

Example B-2

Study of the Anti-Odor Effects (on Incubated Sweat) of Compound 1

The deodorant activity was evaluated in the ex-vivo olfactory evaluation test, on incubated sweat.

Tryptophan ethyl ester hydrochloride (compound 1 of the example A-1) was evaluated at various concentrations in a pool of fresh sweat.

The samples were prepared in 10-ml headspace screw bottles, they are incubated at 35° C. for 24 h under stirring. A sample of sweat with 1 mg of anhydrous aluminum hydroxychloride (ACH) in 1 ml of sweat (i.e. 0.1%) is incubated in order to serve as a positive reference (little odor) and a sample of sweat alone is incubated to serve as a negative reference (unpleasant odor).

The samples after incubation are evaluated olfactively by a panel of several people in a blind test on the headspace bottles. The incubated samples of sweat containing ACH and sweat alone are evaluated at the same time in order to be used respectively as negative and positive references.

3 parameters are evaluated on a scale from 0 to 10:
The residual of the unpleasant odor with 0 for not very unpleasant (positive reference) and 10 for very unpleasant odor (negative reference).
The total power of the odor with 0 for little power and 10 for very powerful.
The pleasantness of the odor with 0 for not very pleasant and 10 for very pleasant.

Table 1 hereinbelow provides the results of the evaluations carried out by a panel of 6 people.

TABLE 1

| Sample | Power | Residual unpleasant odor |
| --- | --- | --- |
| Incubated sweat | 9 | 10 |
| Incubated sweat + ACH | 1.6 | 0.5 |
| Tryptophan ethyl ester hydrochloride 0.1% | 3.2 | 3.4 |
| Tryptophan ethyl ester hydrochloride 0.5% | 2.8 | 3.2 |
| Tryptophan ethyl ester hydrochloride 1% | 1.4 | 0.6 |

A clear decrease in the unpleasant odor was observed with Tryptophan ethyl ester hydrochloride (compound 1 of the example A-1) with respect to the negative reference.

Example B-3

Comparative Study of the Anti-Odor Effects (on Incubated Sweat)

The action of the compound 1 was compared with that of ethyl N-acetyl-L-tryptophanate (compound 2 outside the invention) in incubated sweat. The results show the superiority of the compound 1 with respect to ethyl N-acetyl-L-tryptophanate at several concentrations on the inhibition of the formation of the unpleasant odor in the olfactive evaluation test ex-vivo, on incubated sweat.

The activities of the Tryptophan ethyl ester hydrochloride and of ethyl N-acetyl-L-tryptophanate in incubated sweat were gather together in the following table 2 indicating the results of the evaluations carried out by a panel of 6 people.

TABLE 2

| Sample | Power | Residual unpleasant odor |
| --- | --- | --- |
| Incubated sweat | 9 | 10 |
| Incubated sweat + ACH | 1.6 | 0.5 |
| Tryptophan ethyl ester hydrochloride 0.1% | 3.2 | 3.4 |
| Tryptophan ethyl ester hydrochloride 0.5% | 2.8 | 3.2 |
| Tryptophan ethyl ester hydrochloride 1% | 1.4 | 0.6 |
| Ethyl N-acetyl-L-tryptophanate 0.1% | 6.2 | 6.8 |
| Ethyl N-acetyl-L-tryptophanate 0.5% | 6.8 | 7.5 |
| Ethyl N-acetyl-L-tryptophanate 1% | 6.6 | 7 |

At an equivalent dose, the Ethyl N-acetyl-L-tryptophanate was not as effective as Tryptophan ethyl ester hydrochloride. Tryptophan ester hydrochloride advantageously has better anti-odor activity than the Ethyl N-acetyl-L-tryptophanate.

Example B-3

Study of the Anti-Odor Effects (on Incubated Sweat) of Compounds 3, 4, 5, 6, 7, and 8

The anti-odor activity was evaluated for Tryptophan cis-3-hexenyl ester (compound 3: example A-3), Tryptophan cis-3-hexenyl ester hydrochloride (compound 4, example A-4) and of tryptophan dihydromyrcenyl ester (compound 5: example A-5) at 0.5% in incubated sweat, as well as for the compound 6 at 0.3% in incubated sweat. Furthermore, the Tryptophan benzyl ester and Tryptophan tertiobutyl ester hydrochloride (compounds 7 and 8: example A-6) were evaluated at 0.5% in the incubated sweat.

Table no. 3 hereinbelow indicates the results of the evaluations carried out by a panel of 6 people on the tryptophan cis-3-hexenyl ester (compound 3), of the Tryptophan cis-3-hexenyl hydrochloride (compound 4) and of the tryptophan dihydromyrcenyl ester (compound 5) at 0.5% in the incubated sweat.

TABLE 3

| Sample | Power | Residual unpleasant odor | Pleasantness of the odor |
| --- | --- | --- | --- |
| Incubated sweat | 7 | 9.8 | 0.3 |
| Incubated sweat + ACH | 0.8 | 0.3 | 4 |
| Tryptophan cis-3-hexenyl 0.5% | 6.8 | 1 | 7.8 |
| Tryptophan cis-3-hexenyl hydrochloride 0.5% | 7 | 2.5 | 6 |
| Tryptophan dihydromycenyl ester 0.5% | 5.5 | 2.5 | 5.8 |

Compounds 3, 4 and 5 have an effect of reducing the unpleasant odor compared to the negative control. Moreover, they advantageously contribute to the pleasantness of the odor through the release of odorous volatile molecules.

Table no. 4 hereinbelow indicates the results of the evaluations of the compound 6 at 0.3% in the incubated sweat.

TABLE 4

| Sample | Power | Residual unpleasant odor | Pleasantness of the odor |
| --- | --- | --- | --- |
| Incubated sweat | 7.7 | 8 | 1 |
| Incubated sweat + ACH | 2.7 | 2.7 | 3.7 |
| Tryptophan ethyl ester hydrochloride 0.3% | 3 | 1.7 | 5.3 |
| Tryptophan octyl ester hydrochloride 0.3% | 7 | 0.3 | 7 |

Table no. 5 hereinbelow indicates the results of the valuations of Tryptophan benzyl ester and Tryptophan tertiobutyl ester hydrochloride at 0.5% in the incubated sweat compared with the Tryptophan ethyl ester hydrochloride 1 and Tryptophan ethyl octyl hydrochloride at 0.5% in the incubated sweat.

TABLE 5

| Sample | Power | Residual unpleasant odor | Pleasantness of the odor |
| --- | --- | --- | --- |
| Incubated sweat | 9.3 | 9.7 | 0.3 |
| Incubated sweat + ACH | 2 | 1.7 | 5 |
| Tryptophan ethyl ester hydrochloride 0.5% | 3.3 | 1.3 | 5.7 |
| Tryptophan octyl ester hydrochloride 0.5% | 6.3 | 0.3 | 7.7 |
| Tryptophan benzyl ester 0.5% | 4.3 | 3 | 3.7 |
| Tryptophan tertio butyl ester hydrochloride 0.5% | 4 | 1.7 | 5.7 |

Tryptophan octyl ester hydrochloride has an effect of reducing the unpleasant odor compared to the negative control. Furthermore, it also generates a pleasant odor due to the release of odorous volatile molecules.

Tryptophane benzyl ester and Tryptophan tertio butyl ester hydrochloride have an effect on the reduction of the unpleasant odor compared to the negative control and generate a pleasant odor due to the release of odorous volatile molecules.

C. Formulations

The following formulations were prepared:

Formulation 1:

| Ingredients | % by weight compared to the total weight of the composition |
|---|---|
| Cross-linked Poly(acrylic acid) (Carbomer) | 0.3 |
| Preservatives | 1 |
| Compound 1 | 0.1 |
| Water | qsp | qsp: in sufficient quantities

The formulation produces a deodorant effect.

Formulation 2:

| Ingredients | % by weight compared to the total weight of the composition |
|---|---|
| Cross-linked Poly(acrylic acid) (Carbomer) | 0.3 |
| Preservatives | 1 |
| Compound 1 | 5 |
| Water | qs 100 |

The formulation produces a deodorant effect.

Formulation 3 (with an Additional Antiperspirant Agent):

| Ingredients | % by weight compared to the total weight of the composition |
|---|---|
| Cross-linked Poly(acrylic acid) (Carbomer) | 0.3 |
| Preservatives | 1 |
| Aluminum chlorhydroxide 50% | 18 |
| Aluminum chloride hexahydrate 50% | 6 |
| Compound 1 | 0.1 |
| Water | qs 100 |

The product formulation produces a deodorant and antiperspirant effect.

Formulation 4 (with an Additional Antiperspirant Agent):

| Ingredients | % by weight compared to the total weight of the composition |
|---|---|
| Cross-linked Poly(acrylic acid) (Carbomer) | 0.3 |
| Preservatives | 1 |
| Aluminum chlorhydroxide 50% | 15 |
| Aluminum chloride hexahydrate 50% | 8 |
| Compound 1 | 5 |
| Water | qs 100 |

The product formulation produces a deodorant and antiperspirant effect.

Formulation 5 (Anydrous Formula):

| Ingredients | % by weight compared to the total weight of the composition |
|---|---|
| DIMETHICONE DIMETHICONOL | 11 |
| MODIFIED HECTORITE | 2.66 |
| PROPYLENE CARBONATE | 0.89 |
| ISOPROPYL PALMITATE | 6 |
| Compound 1 | 5 |
| ISODODECANE | 20 |
| DIMETHICONE | Qs 100 |

The formulation produces a deodorant effect.

The invention claimed is:

1. A method for treating body odor which comprises applying to human keratin material at least one compound having formula (I), a salt thereof, an optical isomer thereof, a geometric isomer thereof, a solvate thereof, or mixture thereof, as a deodorant agent:

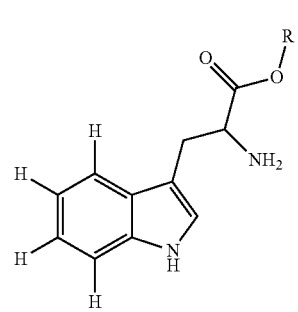

(I)

wherein R represents one of the following radicals:

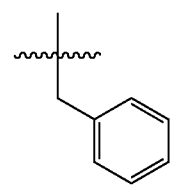

(h)

(aj)

(ak)

2. The method according to claim 1, where the at least one compound having formula (I) is selected from the group consisting of the following compounds:

Tryptophan ethyl ester hydrochloride of the following structure:

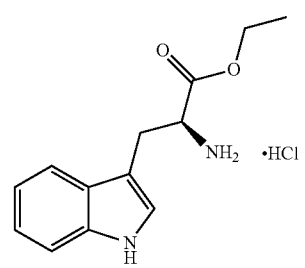

(1)

Tryptophan cis-3-hexenyl ester of the following structure:

(3)

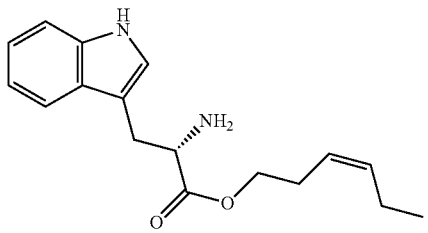

Tryptophan cis-3-hexenyl ester hydrochloride of the following structure:

(4)

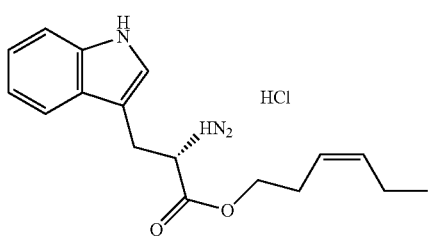

Tryptophan benzyl ester of structure:

(7)

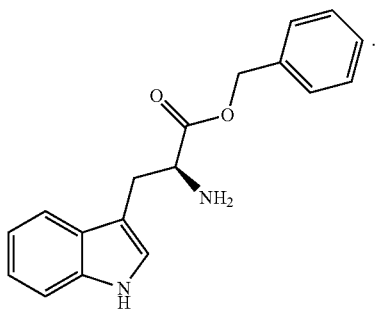

3. The method according to claim 1, where the at least one compound selected from the group consisting of the following compounds:

Tryptophan cis-3-hexenyl ester of the following structure:

(3)

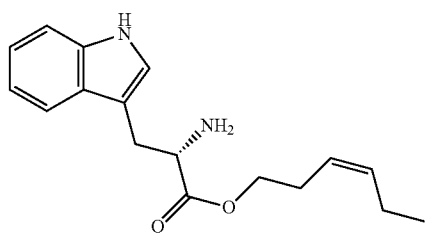

Tryptophan cis-3-hexenyl ester hydrochloride of the following structure:

(4)

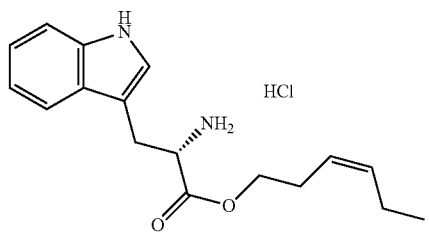

Tryptophan benzyl ester of structure:

(7)

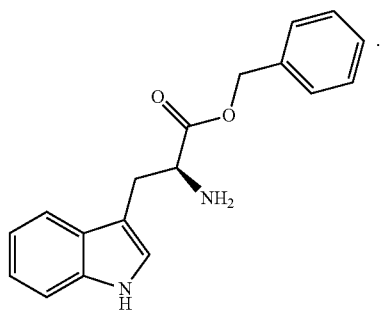

4. The method according to claim 1, wherein R is

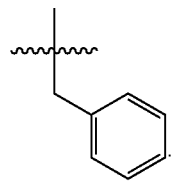 [SMILES: *Cc1ccccc1]

5. The method according to claim 1, wherein R is —$CH_2$—$CH_3$.

6. The method according to claim 1, wherein R is —$CH_2$—$CH_2$—CH=CH—$CH_2$—$CH_3$.

* * * * *